(12) United States Patent
Yuan et al.

(10) Patent No.: US 10,604,763 B2
(45) Date of Patent: Mar. 31, 2020

(54) PROCESSES AND PRODUCTS FOR ENHANCED BIOLOGICAL PRODUCT

(71) Applicant: THE TEXAS A & M UNIVERSITY SYSTEM, College Station, TX (US)

(72) Inventors: Shuhua Yuan, College Station, TX (US); Xin Wang, College Station, TX (US)

(73) Assignee: The Texas A & M University System, College Station, TX (US)

(*) Notice: Subject to any disclaimer, the term of this patent is extended or adjusted under 35 U.S.C. 154(b) by 65 days.

(21) Appl. No.: 15/501,822

(22) PCT Filed: Aug. 6, 2015

(86) PCT No.: PCT/GB2015/052279
§ 371 (c)(1),
(2) Date: Feb. 3, 2017

(87) PCT Pub. No.: WO2016/020689
PCT Pub. Date: Feb. 11, 2016

(65) Prior Publication Data
US 2017/0226526 A1 Aug. 10, 2017

Related U.S. Application Data

(60) Provisional application No. 62/034,133, filed on Aug. 6, 2014.

(51) Int. Cl.
*C12N 15/82* (2006.01)
*C12N 9/10* (2006.01)
*C12N 9/16* (2006.01)

(52) U.S. Cl.
CPC ....... *C12N 15/8243* (2013.01); *C12N 9/1051* (2013.01); *C12N 9/1085* (2013.01); *C12N 9/16* (2013.01); *C12N 15/8221* (2013.01); *C12N 15/8257* (2013.01); *C12Y 204/01213* (2013.01); *C12Y 205/0101* (2013.01); *C12Y 205/01021* (2013.01); *C12Y 301/07011* (2015.07)

(58) Field of Classification Search
CPC .......................... C12N 15/8243; C12N 9/1051
See application file for complete search history.

(56) References Cited

FOREIGN PATENT DOCUMENTS

| WO | 9949063 A1 | 9/1999 |
|---|---|---|
| WO | 2010104763 A1 | 9/2010 |
| WO | 2013033369 A2 | 3/2013 |

OTHER PUBLICATIONS

Ling, H., Biologia (2007); vol. 62, No. 2; pp. 119-123 (Year: 2007).*
Shuiqin, W. et al. Planta, Sep. 2012; vol. 236, No. 3, pp. 1-19. (Year: 2012).*
Search Report and Written Opinion of the International Searching Authority (ISA/EP) for PCT/GB2015/052279 dated Oct. 5, 2015.
Ling, Olefin fusion expression systems for the production of recombinant proteins, Biologia, Apr. 1, 2017, vol. 62, No. 2, pp. 119-123.
Chiang, Selective internalization of self-assembled artificial oil bodies by HER2/neu-positive cells, Nanotechnology, 2011, vol. 22, 015102, pp. 1-11.
Murphy, Structure, Function and Biogenesis of Storage Lipid Bodies and Oleosins in Plants, Lipid Res., 1993, vol. 2, No. 3, pp. 247-280.

* cited by examiner

*Primary Examiner* — Russell Kallis
(74) *Attorney, Agent, or Firm* — Reising Ethington P.C.

(57) ABSTRACT

The invention relates to genetic constructs encoding a compartmenting peptide, wherein expression of the compartmenting peptide leads to formation of a droplet body comprising a targeted biological product, and to vectors including such constructs. The invention also relates to methods of increasing the yield of a biological product in a plant, and to methods for producing a transgenic plant which produces an increased yield of a biological product. The invention also relates to transgenic plants, host cells, plant propagation products and plant parts. The invention also relates to the biological products themselves, produced according to the invention.

14 Claims, 12 Drawing Sheets
Specification includes a Sequence Listing.

SEQUENCE LISTING

```
<160> NUMBER OF SEQ ID NOS: 10

<210> SEQ ID NO 1
<211> LENGTH: 2897
<212> TYPE: DNA
```

<213> ORGANISM: Artificial Sequence
<220> FEATURE:
<223> OTHER INFORMATION: Construct with transit signal peptide and oleosin

<400> SEQUENCE: 1

| | | | | | |
|---|---|---|---|---|---|
| aatcccacaa | aaatctgagc | ttaacagcac | agttgctcct | ctcagagcag | aatcgggtat | 60 |
| tcaacaccct | catatcaact | actacgttgt | gtataacggt | ccacatgccg | gtatatacga | 120 |
| tgactggggt | tgtacaaagg | cggcaacaaa | cggcgttccc | ggagttgcac | acaagaaatt | 180 |
| tgccactatt | acagaggcaa | gagcagcagc | tgacgcgtac | acaacaagtc | agcaaacaga | 240 |
| caggttgaac | ttcatcccca | aaggagaagc | tcaactcaag | cccaagagct | ttgctaaggc | 300 |
| cctaacaagc | ccaccaaagc | aaaaagccca | ctggctcacg | ctaggaacca | aaaggcccag | 360 |
| cagtgatcca | gccccaaaag | agatctcctt | tgccccggag | attacaatgg | acgatttcct | 420 |
| ctatctttac | gatctaggaa | ggaagttcga | aggtgaaggt | gacgacacta | tgttcaccac | 480 |
| tgataatgag | aaggttagcc | tcttcaattt | cagaaagaat | gctgacccac | agatggttag | 540 |
| agaggcctac | gcagcaggtc | tcatcaagac | gatctacccg | agtaacaatc | tccaggagat | 600 |
| caaatacctt | cccaagaagg | ttaaagatgc | agtcaaaaga | ttcaggacta | attgcatcaa | 660 |
| gaacacagag | aaagacatat | ttctcaagat | cagaagtact | attccagtat | ggacgattca | 720 |
| aggcttgctt | cataaaccaa | ggcaagtaat | agagattgga | gtctctaaaa | aggtagttcc | 780 |
| tactgaatct | aaggccatgc | atggagtcta | agattcaaat | cgaggatcta | acagaactcg | 840 |
| ccgtgaagac | tggcgaacag | ttcatacaga | gtcttttacg | actcaatgac | aagaagaaaa | 900 |
| tcttcgtcaa | catggtggag | cacgacactc | tggtctactc | caaaaatgtc | aaagatacag | 960 |
| tctcagaaga | ccaaagggct | attgagactt | tcaacaaag | gataatttcg | ggaaacctcc | 1020 |
| tcggattcca | ttgcccagct | atctgtcact | tcatcgaaag | gacagtagaa | aaggaaggtg | 1080 |
| gctcctacaa | atgccatcat | tgcgataaag | gaaaggctat | cattcaagat | ctctctgccg | 1140 |
| acagtggtcc | caaagatgga | cccccaccca | cgaggagcat | cgtggaaaaa | gaagacgttc | 1200 |
| caaccacgtc | ttcaaagcaa | gtggattgat | gtgacatctc | cactgacgta | agggatgacg | 1260 |
| cacaatccca | ctatccttcg | caagaccctt | cctctatata | aggaagttca | tttcatttgg | 1320 |
| agaggacacg | ctcgagatca | caagtttgta | caaaaaagca | ggctccgcgg | ccgcccccTT | 1380 |
| caccatggct | tcctctgtta | tttcctctgc | agctgttgct | acacgcacca | atgttacaca | 1440 |
| agctggcagc | atgattgcac | ctttcactgg | tctcaaatct | gctgctactt | tccctgtttc | 1500 |
| aaggaagcaa | aaccttgaca | tcacttccat | tgctagcaat | ggtggacgcg | tcagatgcgg | 1560 |
| atccatggcg | gatacagcta | gaggaaccca | tcacgatatc | atcggcagag | accagtaccc | 1620 |
| gatgatgggc | cgagaccgag | accagtacca | gatgtccgga | cgaggatctg | actactccaa | 1680 |
| gtctaggcag | attgctaaag | ctgcaactgc | tgtcacagct | ggtggttccc | tccttgttct | 1740 |
| ctccagcctt | acccttgttg | aactgtcat | agctttgact | gttgcaacac | ctctgctcgt | 1800 |
| tatcttcagc | ccaatccttg | tcccggctct | catcacagtt | gcactcctca | tcaccggttt | 1860 |
| tctttcctct | ggagggtttg | gcattgccgc | tataaccgtt | ttctcttgga | tttacaagta | 1920 |
| cgcaacggga | gagcacccac | agggatcaga | caagttggac | agtgcaagga | tgaagttggg | 1980 |
| aagcaaagct | caggatctga | agacagagc | tcagtactac | ggacagcaac | atactggtgg | 2040 |
| ggaacatgac | cgtgaccgta | tcgtggtgg | ccagcacact | acttaaggta | ccttaagggt | 2100 |
| gggcgcgccg | acccagcttt | cttgtacaaa | gtggtgccta | ggtgagtcta | gagagttaat | 2160 |

```
taagacccgg gactagtccc tagagtcctg ctttaatgag atatgcgaga cgcctatgat   2220
cgcatgatat ttgctttcaa ttctgttgtg cacgttgtaa aaaacctgag catgtgtagc   2280
tcagatcctt accgccggtt tcggttcatt ctaatgaata tatcacccgt tactatcgta   2340
tttttatgaa taatattctc cgttcaattt actgattgta ccctactact tatatgtaca   2400
atattaaaat gaaaacaata tattgtgctg aataggttta tagcgacatc tatgatagag   2460
cgccacaata acaaacaatt gcgttttatt attacaaatc caattttaaa aaaagcggca   2520
gaaccggtca aacctaaaag actgattaca taaatcttat tcaaatttca aaagtgcccc   2580
aggggctagt atctacgaca caccgagcgg cgaactaata acgctcactg aagggaactc   2640
cggttccccg ccggcgcgca tgggtgagat tccttgaagt tgagtattgg ccgtccgctc   2700
taccgaaagt tacgggcacc attcaacccg gtccagcacg gcggccgggt aaccgacttg   2760
ctgccccgag aattatgcag cattttttg gtgtatgtgg gccccaaatg aagtgcaggt   2820
caaaccttga cagtgacgac aaatcgttgg gcgggtccag ggcgaatttt gcgacaacat   2880
gtcgaggctc agcagga                                                 2897
```

<210> SEQ ID NO 2
<211> LENGTH: 233
<212> TYPE: PRT
<213> ORGANISM: Artificial Sequence
<220> FEATURE:
<223> OTHER INFORMATION: Transit signal peptide and oleosin

<400> SEQUENCE: 2

```
Met Ala Ser Ser Val Ile Ser Ser Ala Ala Val Ala Thr Arg Thr Asn
1               5                   10                  15

Val Thr Gln Ala Gly Ser Met Ile Ala Pro Phe Thr Gly Leu Lys Ser
            20                  25                  30

Ala Ala Thr Phe Pro Val Ser Arg Lys Gln Asn Leu Asp Ile Thr Ser
        35                  40                  45

Ile Ala Ser Asn Gly Gly Arg Val Arg Cys Gly Ser Met Ala Asp Thr
    50                  55                  60

Ala Arg Gly Thr His His Asp Ile Ile Gly Arg Asp Gln Tyr Pro Met
65                  70                  75                  80

Met Gly Arg Asp Arg Asp Gln Tyr Gln Met Ser Gly Arg Gly Ser Asp
                85                  90                  95

Tyr Ser Lys Ser Arg Gln Ile Ala Lys Ala Ala Thr Ala Val Thr Ala
            100                 105                 110

Gly Gly Ser Leu Leu Val Leu Ser Ser Leu Thr Leu Val Gly Thr Val
        115                 120                 125

Ile Ala Leu Thr Val Ala Thr Pro Leu Leu Val Ile Phe Ser Pro Ile
    130                 135                 140

Leu Val Pro Ala Leu Ile Thr Val Ala Leu Leu Ile Thr Gly Phe Leu
145                 150                 155                 160

Ser Ser Gly Gly Phe Gly Ile Ala Ala Ile Thr Val Phe Ser Trp Ile
                165                 170                 175

Tyr Lys Tyr Ala Thr Gly Glu His Pro Gln Gly Ser Asp Lys Leu Asp
            180                 185                 190

Ser Ala Arg Met Lys Leu Gly Ser Lys Ala Gln Asp Leu Lys Asp Arg
        195                 200                 205

Ala Gln Tyr Tyr Gly Gln Gln His Thr Gly Gly Glu His Asp Arg Asp
    210                 215                 220

Arg Thr Arg Gly Gly Gln His Thr Thr
```

225         230

<210> SEQ ID NO 3
<211> LENGTH: 3324
<212> TYPE: DNA
<213> ORGANISM: Artificial Sequence
<220> FEATURE:
<223> OTHER INFORMATION: Construct with transit signal peptide,
      truncated oleosin, and green fluorescence protein.

<400> SEQUENCE: 3

| | | | | | |
|---|---|---|---|---|---|
| aatcccacaa | aaatctgagc | ttaacagcac | agttgctcct | ctcagagcag | aatcgggtat | 60 |
| tcaacaccct | catatcaact | actacgttgt | gtataacggt | ccacatgccg | gtatatacga | 120 |
| tgactggggt | tgtacaaagg | cggcaacaaa | cggcgttccc | ggagttgcac | acaagaaatt | 180 |
| tgccactatt | acagaggcaa | gagcagcagc | tgacgcgtac | acaacaagtc | agcaaacaga | 240 |
| caggttgaac | ttcatcccca | aggagaagc | tcaactcaag | cccaagagct | tgctaaggc | 300 |
| cctaacaagc | ccaccaaagc | aaaaagccca | ctggctcacg | ctaggaacca | aaaggcccag | 360 |
| cagtgatcca | gccccaaaag | agatctcctt | tgccccggag | attacaatgg | acgatttcct | 420 |
| ctatctttac | gatctaggaa | ggaagttcga | aggtgaaggt | gacgacacta | tgttcaccac | 480 |
| tgataatgag | aaggttagcc | tcttcaattt | cagaaagaat | gctgacccac | agatggttag | 540 |
| agaggcctac | gcagcaggtc | tcatcaagac | gatctacccg | agtaacaatc | tccaggagat | 600 |
| caaataccct | cccaagaagg | ttaaagatgc | agtcaaaaga | ttcaggacta | attgcatcaa | 660 |
| gaacacagag | aaagacatat | ttctcaagat | cagaagtact | attccagtat | ggacgattca | 720 |
| aggcttgctt | cataaaccaa | ggcaagtaat | agagattgga | gtctctaaaa | aggtagttcc | 780 |
| tactgaatct | aaggccatgc | atggagtcta | agattcaaat | cgaggatcta | acagaactcg | 840 |
| ccgtgaagac | tggcgaacag | ttcatacaga | gtctttttacg | actcaatgac | aagaagaaaa | 900 |
| tcttcgtcaa | catggtggag | cacgacactc | tggtctactc | caaaaatgtc | aaagatacag | 960 |
| tctcagaaga | ccaaagggct | attgagactt | ttcaacaaag | gataatttcg | ggaaacctcc | 1020 |
| tcggattcca | ttgcccagct | atctgtcact | tcatcgaaag | gacagtagaa | aaggaaggtg | 1080 |
| gctcctacaa | atgccatcat | tgcgataaag | gaaaggctat | cattcaagat | ctctctgccg | 1140 |
| acagtggtcc | caagatgga | cccccaccca | cgaggagcat | cgtggaaaaa | gaagacgttc | 1200 |
| caaccacgtc | ttcaaagcaa | gtggattgat | gtgacatctc | cactgacgta | agggatgacg | 1260 |
| cacaatccca | ctatccttcg | caagacccctt | cctctatata | aggaagttca | tttcatttgg | 1320 |
| agaggacacg | ctcgagatca | caagtttgta | caaaaaagca | ggctccgcgg | ccgccccctt | 1380 |
| caccatggct | tcctctgtta | tttcctctgc | agctgttgct | acacgcacca | atgttacaca | 1440 |
| agctggcagc | atgattgcac | ctttcactgg | tctcaaatct | gctgctactt | tccctgtttc | 1500 |
| aaggaagcaa | aaccttgaca | tcacttccat | tgctagcaat | ggtggacgcg | tcagatgcgg | 1560 |
| atccatgaaa | gctgcaactg | ctgtcacagc | tggtggttcc | ctccttgttc | tctccagcct | 1620 |
| taccccttgtt | ggaactgtca | tagctttgac | tgttgcaaca | cctctgctcg | ttatcttcag | 1680 |
| cccaatcctt | gtcccggctc | tcatcacagt | tgcactcctc | atcaccggtt | ttctttcctc | 1740 |
| tggagggttt | ggcattgccg | ctataaccgt | tttctcttgg | atttacgtcg | acctgcagat | 1800 |
| gagtaaagga | gaagaacttt | tcactggagt | tgtcccaatt | cttgttgaat | tagatggtga | 1860 |
| tgttaatggg | cacaaatttt | ctgtcagtgg | agagggtgaa | ggtgatgcaa | catacggaaa | 1920 |
| acttacccctt | aaatttattt | gcactactgg | aaaactacct | gttccatggc | caacacttgt | 1980 |

```
cactactttc acttatggtg ttcaatgctt ttcaagatac ccagatcata tgaagcggca    2040
cgacttcttc aagagcgcca tgcctgaggg atacgtgcag gagaggacca tctctttcaa    2100
ggacgacggg aactacaaga cacgtgctga agtcaagttt gagggagaca ccctcgtcaa    2160
caggatcgag cttaagggaa tcgatttcaa ggaggacgga acatcctcg gccacaagtt     2220 ggaatacaac tacaactccc acaacgtata catcacggca gacaaacaaa agaatggaat    2280
caaagctaac ttcaaaatta gacacaacat tgaagatgga agcgttcaac tagcagacca    2340
ttatcaacaa aatactccaa ttggcgatgg ccctgtcctt ttaccagaca accattacct    2400
gtccacacaa tctgcccttt cgaaagatcc aacgaaaag agagaccaca tggtccttct      2460
tgagtttgta acagctgctg ggattacaca tggcatggat gaactataca aataagtacc    2520
ttaagggtgg cgcgccgacc cagctttctt gtacaaagtg tgcctaggt gagtctagag      2580 agttaattaa gacccgggac tagtccctag agtcctgctt taatgagata tgcgagacgc    2640
ctatgatcgc atgatatttg ctttcaattc tgttgtgcac gttgtaaaaa acctgagcat    2700
gtgtagctca gatccttacc gccggtttcg gttcattcta atgaatatat cacccgttac    2760
tatcgtattt ttatgaataa tattctccgt tcaatttact gattgtaccc tactacttat    2820
atgtacaata ttaaaatgaa aacaatatat tgtgctgaat aggtttatag cgacatctat    2880
gatagagcgc cacaataaca aacaattgcg ttttattatt acaaatccaa ttttaaaaaa    2940
agcggcagaa ccggtcaaac ctaaaagact gattacataa atcttattca aatttcaaaa    3000
gtgccccagg ggctagtatc tacgacacac cgagcggcga actaataacg ctcactgaag    3060
ggaactccgg ttccccgccg cgcgcatgg gtgagattcc ttgaagttga gtattggccg     3120
tccgctctac cgaaagttac gggcaccatt caacccggtc cagcacggcg gccgggtaac    3180
cgacttgctg ccccgagaat tatgcagcat ttttttggtg tatgtgggcc ccaaatgaag    3240
tgcaggtcaa accttgacag tgacgacaaa tcgttgggcg ggtccagggc gaattttgcg    3300
acaacatgtc gaggctcagc agga                                           3324
```

<210> SEQ ID NO 4
<211> LENGTH: 376
<212> TYPE: PRT
<213> ORGANISM: Artificial Sequence
<220> FEATURE:
<223> OTHER INFORMATION: Transit signal peptide, truncated oleosin, and
      green fluorescence protein

<400> SEQUENCE: 4

```
Met Ala Ser Ser Val Ile Ser Ser Ala Ala Val Ala Thr Arg Thr Asn
1               5                   10                  15

Val Thr Gln Ala Gly Ser Met Ile Ala Pro Phe Thr Gly Leu Lys Ser
            20                  25                  30

Ala Ala Thr Phe Pro Val Ser Arg Lys Gln Asn Leu Asp Ile Thr Ser
        35                  40                  45

Ile Ala Ser Asn Gly Gly Arg Val Arg Cys Gly Ser Met Lys Ala Ala
    50                  55                  60

Thr Ala Val Thr Ala Gly Gly Ser Leu Leu Val Leu Ser Ser Leu Thr
65                  70                  75                  80

Leu Val Gly Thr Val Ile Ala Leu Thr Val Ala Thr Pro Leu Leu Val
                85                  90                  95

Ile Phe Ser Pro Ile Leu Val Pro Ala Leu Ile Thr Val Ala Leu Leu
            100                 105                 110

Ile Thr Gly Phe Leu Ser Ser Gly Gly Phe Gly Ile Ala Ala Ile Thr
```

```
                115                 120                 125
Val Phe Ser Trp Ile Tyr Val Asp Leu Gln Met Ser Lys Gly Glu Glu
        130                 135                 140

Leu Phe Thr Gly Val Val Pro Ile Leu Val Glu Leu Asp Gly Asp Val
145                 150                 155                 160

Asn Gly His Lys Phe Ser Val Ser Gly Glu Gly Glu Gly Asp Ala Thr
                165                 170                 175

Tyr Gly Lys Leu Thr Leu Lys Phe Ile Cys Thr Thr Gly Lys Leu Pro
            180                 185                 190

Val Pro Trp Pro Thr Leu Val Thr Thr Phe Thr Tyr Gly Val Gln Cys
        195                 200                 205

Phe Ser Arg Tyr Pro Asp His Met Lys Arg His Asp Phe Phe Lys Ser
    210                 215                 220

Ala Met Pro Glu Gly Tyr Val Gln Glu Arg Thr Ile Ser Phe Lys Asp
225                 230                 235                 240

Asp Gly Asn Tyr Lys Thr Arg Ala Glu Val Lys Phe Glu Gly Asp Thr
                245                 250                 255

Leu Val Asn Arg Ile Glu Leu Lys Gly Ile Asp Phe Lys Glu Asp Gly
            260                 265                 270

Asn Ile Leu Gly His Lys Leu Glu Tyr Asn Tyr Asn Ser His Asn Val
        275                 280                 285

Tyr Ile Thr Ala Asp Lys Gln Lys Asn Gly Ile Lys Ala Asn Phe Lys
    290                 295                 300

Ile Arg His Asn Ile Glu Asp Gly Ser Val Gln Leu Ala Asp His Tyr
305                 310                 315                 320

Gln Gln Asn Thr Pro Ile Gly Asp Gly Pro Val Leu Leu Pro Asp Asn
                325                 330                 335

His Tyr Leu Ser Thr Gln Ser Ala Leu Ser Lys Asp Pro Asn Glu Lys
            340                 345                 350

Arg Asp His Met Val Leu Leu Glu Phe Val Thr Ala Ala Gly Ile Thr
        355                 360                 365

His Gly Met Asp Glu Leu Tyr Lys
    370                 375

<210> SEQ ID NO 5
<211> LENGTH: 2598
<212> TYPE: DNA
<213> ORGANISM: Artificial Sequence
<220> FEATURE:
<223> OTHER INFORMATION: Construct with transit signal peptide and
      truncated oleosin

<400> SEQUENCE: 5
aatcccacaa aaatctgagc ttaacagcac agttgctcct ctcagagcag aatcgggtat      60
tcaacaccct catatcaact actacgttgt gtataacggt ccacatgccg gtatatacga    120
tgactggggt tgtacaaagg cggcaacaaa cggcgttccc ggagttgcac acaagaaatt    180
tgccactatt acagaggcaa gagcagcagc tgacgcgtac acaacaagtc agcaaacaga    240
caggttgaac ttcatcccca aaggagaagc tcaactcaag cccaagagct tgctaaggc     300 cctaacaagc ccaccaaagc aaaaagccca ctggctcacg ctaggaacca aaaggcccag    360
cagtgatcca gccccaaaag agatctcctt tgccccggag attacaatgg acgatttcct    420
ctatctttac gatctaggaa ggaagttcga aggtgaaggt gacgcactgg ttgttcaccac   480 tgataatgag aaggttagcc tcttcaattt cagaaagaat gctgacccac agatggttag    540
```

```
agaggcctac gcagcaggtc tcatcaagac gatctacccg agtaacaatc tccaggagat    600
caaataccett cccaagaagg ttaaagatgc agtcaaaaga ttcaggacta attgcatcaa    660
gaacacagag aaagacatat ttctcaagat cagaagtact attccagtat ggacgattca    720
aggcttgctt cataaaccaa ggcaagtaat agagattgga gtctctaaaa aggtagttcc    780
tactgaatct aaggccatgc atggagtcta agattcaaat cgaggatcta acagaactcg    840
ccgtgaagac tggcgaacag ttcatacaga gtcttttacg actcaatgac aagaagaaaa    900
tcttcgtcaa catggtggag cacgacactc tggtctactc caaaaatgtc aaagatacag    960
tctcagaaga ccaaagggct attgagactt tcaacaaag gataatttcg ggaaacctcc      1020
tcggattcca ttgcccagct atctgtcact tcatcgaaag gacagtagaa aaggaaggtg    1080
gctcctacaa atgccatcat tgcgataaag gaaaggctat cattcaagat ctctctgccg    1140
acagtggtcc caaagatgga ccccacccca cgaggagcat cgtggaaaaa gaagacgttc    1200
caaccacgtc ttcaaagcaa gtggattgat gtgacatctc cactgacgta agggatgacg    1260
cacaatccca ctatccttcg caagacccett cctctatata aggaagttca tttcatttgg    1320
agaggacacg ctcgagatca caagtttgta caaaaaagca ggctccgcgg ccgccccctt    1380
caccatggct tcctctgtta tttcctctgc agctgttgct acacgcacca atgttacaca    1440
agctggcagc atgattgcac ctttcactgg tctcaaatct gctgctactt ccctgtttc     1500
aaggaagcaa aaccttgaca tcacttccat tgctagcaat ggtggacgcg tcagatgcgg    1560
atccatgaaa gctgcaactg ctgtcacagc tggtggttcc ctccttgttc tctccagcct    1620
taccecettgtt ggaactgtca tagctttgac tgttgcaaca cctctgctcg ttatcttcag    1680
cccaatcett gtcccggctc tcatcacagt tgcactcctc atcaccggtt ttctttcctc    1740
tggagggttt ggcattgccg ctataaccgt tttctcttgg atttactaag taccttaagg    1800
gtggcgcgcc gacccagctt tcttgtacaa agtggtgcct aggtgagtct agagagttaa    1860
ttaagacccg ggactagtcc ctagagtcct gctttaatga gatatgcgag acgcctatga    1920
tcgcatgata tttgctttca attctgttgt gcacgttgta aaaaacctga gcatgtgtag    1980
ctcagatcct taccgccggt ttcggttcat tctaatgaat atatcacccg ttactatcgt    2040
attttttatga ataatattct ccgttcaatt tactgattgt accctactac ttatatgtac    2100
aatattaaaa tgaaaacaat atattgtgct gaataggttt atagcgacat ctatgataga    2160
gcgccacaat aacaaacaat tgcgttttat tattacaaat ccaattttaa aaaaagcggc    2220
agaaccggtc aaacctaaaa gactgattac ataaatctta ttcaaatttc aaaagtgccc    2280
caggggctag tatctacgac acaccgagcg gcgaactaat aacgctcact gaagggaact    2340
ccggttcccc gccggcgcgc atgggtgaga ttccttgaag ttgagtattg gccgtccgct    2400
ctaccgaaag ttacgggcac cattcaaccc ggtccagcac ggcggccggg taaccgactt    2460
gctgccccga gaattatgca gcattttttt ggtgtatgtg ggccccaaat gaagtgcagg    2520
tcaaaccttg acagtgacga caaatcgttg ggcgggtcca gggcgaattt tgcgacaaca    2580
tgtcgaggct cagcagga                                                  2598
```

<210> SEQ ID NO 6
<211> LENGTH: 134
<212> TYPE: PRT
<213> ORGANISM: Artificial Sequence
<220> FEATURE:
<223> OTHER INFORMATION: Transit signal peptide and truncated oleosin

<400> SEQUENCE: 6

```
Met Ala Ser Ser Val Ile Ser Ser Ala Ala Val Ala Thr Arg Thr Asn
1               5                   10                  15

Val Thr Gln Ala Gly Ser Met Ile Ala Pro Phe Thr Gly Leu Lys Ser
            20                  25                  30

Ala Ala Thr Phe Pro Val Ser Arg Lys Gln Asn Leu Asp Ile Thr Ser
        35                  40                  45

Ile Ala Ser Asn Gly Gly Arg Val Arg Cys Gly Ser Met Lys Ala Ala
    50                  55                  60

Thr Ala Val Thr Ala Gly Gly Ser Leu Leu Val Leu Ser Ser Leu Thr
65                  70                  75                  80

Leu Val Gly Thr Val Ile Ala Leu Thr Val Ala Thr Pro Leu Leu Val
            85                  90                  95

Ile Phe Ser Pro Ile Leu Val Pro Ala Leu Ile Thr Val Ala Leu Leu
                100                 105                 110

Ile Thr Gly Phe Leu Ser Ser Gly Gly Phe Gly Ile Ala Ala Ile Thr
            115                 120                 125

Val Phe Ser Trp Ile Tyr
    130

<210> SEQ ID NO 7
<211> LENGTH: 3623
<212> TYPE: DNA
<213> ORGANISM: Artificial Sequence
<220> FEATURE:
<223> OTHER INFORMATION: Construct with transit signal peptide, oleosin
      and green fluorescence protein

<400> SEQUENCE: 7
aatcccacaa aaatctgagc ttaacagcac agttgctcct ctcagagcag aatcgggtat      60
tcaacaccct catatcaact actacgttgt gtataacggt ccacatgccg gtatatacga    120
tgactggggt tgtacaaagg cggcaacaaa cggcgttccc ggagttgcac acaagaaatt    180
tgccactatt acagaggcaa gagcagcagc tgacgcgtac acaacaagtc agcaaacaga    240
caggttgaac ttcatcccca aggagaagc tcaactcaag cccaagagct tgctaaggc     300 cctaacaagc ccaccaaagc aaaaagccca ctggctcacg ctaggaacca aaaggcccag    360
cagtgatcca gccccaaaag agatctcctt tgccccggag attacaatgg acgatttcct    420
ctatctttac gatctaggaa ggaagttcga aggtgaaggt gacgcactta tgttcaccac    480
tgataatgag aaggttagcc tcttcaattt cagaaagaat gctgacccac agatggttag    540
agaggcctac gcagcaggtc tcatcaagac gatctacccg agtaacaatc tccaggagat    600
caaatacctt cccaagaagg ttaaagatgc agtcaaaaga ttcaggacta attgcatcaa    660
gaacacagag aaagacatat ttctcaagat cagaagtact attccagtat ggacgattca    720
aggcttgctt cataaaccaa ggcaagtaat agagattgga gtctctaaaa aggtagttcc    780
tactgaatct aaggccatgc atggagtcta agattcaaat cgaggatcta acagaactcg    840
ccgtgaagac tggcgaacag ttcatacaga gtctttttacg actcaatgac aagaagaaaa    900
tcttcgtcaa catggtggag cacgacactc tggtctactc caaaaatgtc aaagatacag    960
tctcagaaga ccaaagggct attgagactt ttcaacaaag ataatttcg ggaaacctcc    1020 tcggattcca ttgcccagct atctgtcact tcatcgaaag gacagtagaa aaggaaggtg   1080
gctcctacaa atgccatcat tgcgataaag gaaaggctat cattcaagat ctctctgccg   1140
acagtggtcc caaagatgga cccccaccca cgaggagcat cgtggaaaaa gaagacgttc   1200
```

```
caaccacgtc ttcaaagcaa gtggattgat gtgacatctc cactgacgta agggatgacg    1260
cacaatccca ctatccttcg caagacccett cctctatata aggaagttca tttcatttgg    1320
agaggacacg ctcgagatca caagtttgta caaaaaagca ggctccgcgg ccgccccctt    1380
caccatggct tcctctgtta tttcctctgc agctgttgct acacgcacca atgttacaca    1440
agctggcagc atgattgcac cttttcactgg tctcaaatct gctgctactt tccctgtttc    1500
aaggaagcaa aaccttgaca tcacttccat tgctagcaat ggtggacgcg tcagatgcgg    1560
atccatggcg gatacagcta gaggaaccca tcacgatatc atcggcagag accagtaccc    1620
gatgatgggc cgagaccgag accagtacca gatgtccgga cgaggatctg actactccaa    1680
gtctaggcag attgctaaag ctgcaactgc tgtcacagct ggtggttccc tccttgttct    1740
ctccagcctt acccttgttg gaactgtcat agctttgact gttgcaacac ctctgctcgt    1800
tatcttcagc ccaatccttg tcccggctct catcacagtt gcactcctca tcaccggttt    1860
tctttcctct ggagggtttg gcattgccgc tataaccgtt ttctcttgga tttacaagta    1920
cgcaacggga gagcacccac agggatcaga caagttggac agtgcaagga tgaagttggg    1980
aagcaaagct caggatctga agacagagc tcagtactac ggacagcaac atactggtgg    2040
ggaacatgac cgtgaccgta ctcgtggtgg ccagcacact actgtcgacc tgcagatgag    2100
taaaggagaa gaacttttca ctggagttgt cccaattctt gttgaattag atggtgatgt    2160
taatgggcac aaattttctg tcagtgggaga gggtgaaggt gatgcaacat acggaaaact    2220
taccctaaaa tttatttgca ctactggaaa actacctgtt ccatggccaa cacttgtcac    2280
tactttcact tatggtgttc aatgcttttc aagataccca gatcatatga agcggcacga    2340
cttcttcaag agcgccatgc ctgagggata cgtgcaggag aggaccatct ctttcaagga    2400
cgacgggaac tacaagacac gtgctgaagt caagtttgag ggagacaccc tcgtcaacag    2460
gatcgagctt aagggaatcg atttcaagga ggacggaaac atcctcggcc acaagttgga    2520
atacaactac aactcccaca acgtatacat cacggcagac aaacaaaaga atggaatcaa    2580
agctaacttc aaaattagac acaacattga agatggaagc gttcaactag cagaccatta    2640
tcaacaaaat actccaattg gcgatggccc tgtccttttta ccagacaacc attacctgtc    2700
cacacaatct gccctttcga aagatcccaa cgaaagagaga gaccacatgg tccttcttga    2760
gtttgtaaca gctgctggga ttacacatgg catggatgaa ctatacaaat aaggtacctt    2820
aagggtgggc gcgccgaccc agcttcttg tacaaagtgg tgcctaggtg agtctagaga    2880
gttaattaag acccgggact agtccctaga gtcctgcttt aatgagatat gcagacgcc    2940 tatgatcgca tgatatttgc tttcaattct gttgtgcacg ttgtaaaaaa cctgagcatg    3000
tgtagctcag atccttaccg ccggtttcgg ttcattctaa tgaatatatc cccgttact    3060 atcgtatttt tatgaataat attctccgtt caatttactg attgtaccct actacttata    3120
tgtacaatat aaaatgaaa acaatatatt gtgctgaata ggtttatagc gacatctatg    3180
atagagcgcc acaataacaa acaattgcgt tttattatta caaatccaat tttaaaaaaa    3240
gcggcagaac cggtcaaacc taaaagactg attacataaa tcttattcaa atttcaaaag    3300
tgccccaggg gctagtatct acgacacacc gagcggcgaa ctaataacgc tcactgaagg    3360
gaactccggt tccccgccgg cgcgcatggg tgagattcct tgaagttgag tattggccgt    3420
ccgctctacc gaaagttacg ggcaccattc aacccggtcc agcacggcgg ccgggtaacc    3480
gacttgctgc cccgagaatt atgcagcatt ttttggtgt atgtgggccc caaatgaagt    3540
gcaggtcaaa ccttgacagt gacgacaaat cgttgggcgg gtccagggcg aattttgcga    3600
```

-continued caacatgtcg aggctcagca gga                                                      3623

<210> SEQ ID NO 8
<211> LENGTH: 473
<212> TYPE: PRT
<213> ORGANISM: Artificial Sequence
<220> FEATURE:
<223> OTHER INFORMATION: Transit signal peptide, oleosin and green
      fluorescence protein

<400> SEQUENCE: 8

Met Ala Ser Ser Val Ile Ser Ser Ala Ala Val Ala Thr Arg Thr Asn
1               5                   10                  15

Val Thr Gln Ala Gly Ser Met Ile Ala Pro Phe Thr Gly Leu Lys Ser
            20                  25                  30

Ala Ala Thr Phe Pro Val Ser Arg Lys Gln Asn Leu Asp Ile Thr Ser
        35                  40                  45

Ile Ala Ser Asn Gly Gly Arg Val Arg Cys Gly Ser Ala Asp Thr Ala
    50                  55                  60

Arg Gly Thr His His Asp Ile Ile Gly Arg Asp Gln Tyr Pro Met Met
65                  70                  75                  80

Gly Arg Asp Arg Asp Gln Tyr Gln Met Ser Gly Arg Gly Ser Asp Tyr
                85                  90                  95

Ser Lys Ser Arg Gln Ile Ala Lys Ala Ala Thr Ala Val Thr Ala Gly
            100                 105                 110

Gly Ser Leu Leu Val Leu Ser Ser Leu Thr Leu Val Gly Thr Val Ile
        115                 120                 125

Ala Leu Thr Val Ala Thr Pro Leu Leu Val Ile Phe Ser Pro Ile Leu
    130                 135                 140

Val Pro Ala Leu Ile Thr Val Ala Leu Leu Ile Thr Gly Phe Leu Ser
145                 150                 155                 160

Ser Gly Gly Phe Gly Ile Ala Ala Ile Thr Val Phe Ser Trp Ile Tyr
                165                 170                 175

Lys Tyr Ala Thr Gly Glu His Pro Gln Gly Asp Lys Leu Asp Ser Ala
            180                 185                 190

Arg Met Lys Leu Gly Ser Lys Ala Gln Asp Leu Lys Asp Arg Ala Gln
        195                 200                 205

Tyr Tyr Gly Gln Gln His Thr Gly Gly Glu His Asp Arg Asp Arg Thr
    210                 215                 220

Arg Gly Gly Gln His Thr Thr Val Asp Leu Gln Met Ser Lys Gly Glu
225                 230                 235                 240

Glu Leu Phe Thr Gly Val Val Pro Ile Leu Val Glu Leu Asp Gly Asp
                245                 250                 255

Val Asn Gly His Lys Phe Ser Val Ser Gly Glu Gly Glu Gly Asp Ala
            260                 265                 270

Thr Tyr Gly Lys Leu Thr Leu Lys Phe Ile Cys Thr Thr Gly Lys Leu
        275                 280                 285

Pro Val Pro Trp Pro Thr Leu Val Thr Thr Phe Thr Tyr Gly Val Gln
    290                 295                 300

Cys Phe Ser Arg Tyr Pro Asp His Met Lys Arg His Asp Phe Phe Lys
305                 310                 315                 320

Ser Ala Met Pro Glu Gly Tyr Val Gln Glu Arg Thr Ile Ser Phe Lys
                325                 330                 335

Asp Asp Gly Asn Tyr Lys Thr Arg Ala Glu Val Lys Phe Glu Gly Asp
            340                 345                 350

```
Thr Leu Val Asn Arg Ile Glu Leu Lys Gly Ile Asp Phe Lys Glu Asp
            355                 360                 365

Gly Asn Ile Leu Gly His Lys Leu Glu Tyr Asn Tyr Asn Ser His Asn
        370                 375                 380

Val Tyr Ile Thr Ala Asp Lys Gln Lys Asn Gly Ile Lys Ala Asn Phe
385                 390                 395                 400

Lys Ile Arg His Asn Ile Glu Asp Gly Ser Val Gln Leu Ala Asp His
                405                 410                 415

Tyr Gln Gln Asn Thr Pro Ile Gly Asp Gly Pro Val Leu Leu Pro Asp
                420                 425                 430

Asn His Tyr Leu Ser Thr Gln Ser Ala Leu Ser Lys Asp Pro Asn Glu
            435                 440                 445

Lys Arg Asp His Met Val Leu Leu Glu Phe Val Thr Ala Ala Gly Ile
        450                 455                 460

Thr His Gly Met Asp Glu Leu Tyr Lys
465                 470

<210> SEQ ID NO 9
<211> LENGTH: 173
<212> TYPE: PRT
<213> ORGANISM: Arabidopsis thaliana

<400> SEQUENCE: 9

Met Ala Asp Thr Ala Arg Gly Thr His His Asp Ile Ile Gly Arg Asp
1               5                   10                  15

Gln Tyr Pro Met Met Gly Arg Asp Arg Asp Gln Tyr Gln Met Ser Gly
            20                  25                  30

Arg Gly Ser Asp Tyr Ser Lys Ser Arg Gln Ile Ala Lys Ala Ala Thr
        35                  40                  45

Ala Val Thr Ala Gly Gly Ser Leu Leu Val Leu Ser Ser Leu Thr Leu
    50                  55                  60

Val Gly Thr Val Ile Ala Leu Thr Val Ala Thr Pro Leu Leu Val Ile
65                  70                  75                  80

Phe Ser Pro Ile Leu Val Pro Ala Leu Ile Thr Val Ala Leu Leu Ile
                85                  90                  95

Thr Gly Phe Leu Ser Ser Gly Gly Phe Gly Ile Ala Ala Ile Thr Val
            100                 105                 110

Phe Ser Trp Ile Tyr Lys Tyr Ala Thr Gly Glu His Pro Gln Gly Ser
        115                 120                 125

Asp Lys Leu Asp Ser Ala Arg Met Lys Leu Gly Ser Lys Ala Gln Asp
    130                 135                 140

Leu Lys Asp Arg Ala Gln Tyr Tyr Gly Gln Gln His Thr Gly Gly Glu
145                 150                 155                 160

His Asp Arg Asp Arg Thr Arg Gly Gly Gln His Thr Thr
                165                 170

<210> SEQ ID NO 10
<211> LENGTH: 73
<212> TYPE: PRT
<213> ORGANISM: Arabidopsis thaliana

<400> SEQUENCE: 10

Lys Ala Ala Thr Ala Val Thr Ala Gly Gly Ser Leu Leu Val Leu Ser
1               5                   10                  15

Ser Leu Thr Leu Val Gly Thr Val Ile Ala Leu Thr Val Ala Thr Pro
            20                  25                  30
```

```
Leu Leu Val Ile Phe Ser Pro Ile Leu Val Pro Ala Leu Ile Thr Val
        35                  40                  45

Ala Leu Leu Ile Thr Gly Phe Leu Ser Ser Gly Gly Phe Gly Ile Ala
        50                  55                  60

Ala Ile Thr Val Phe Ser Trp Ile Tyr
65                  70
```

PROCESSES AND PRODUCTS FOR ENHANCED BIOLOGICAL PRODUCT

FIELD

The present invention relates to the field of plant molecular biology, biopharmaceutical production, and plant genetic engineering. More specifically, the present invention relates to the controlled generation of droplet bodies to store high value biological products, such as terpenes, terpenoids and many other compounds.

BACKGROUND

Many terpene and terpenoid compounds are important nutraceuticals and drug precursors. Some terpene or terpenoid compounds can be used for fuels and chemicals. The production of terpene and terpenoid compounds is frequently limited. This limited production may be as a result of product inhibition, where the end product will either be toxic to the cell or as a result of feedback, by an intermediate or end product, to inhibit further production. For this reason, a novel method to compartment terpene would be extremely advantageous. In at least some embodiments, the present invention seeks to both remove the feedback and increase the compartmentation to increase the yield.

SUMMARY

According to a first aspect of the invention, genetic constructs are provided comprising a promoter and a coding sequencing encoding a compartmenting peptide, wherein expression of the compartmenting peptide leads to formation of a droplet body comprising a targeted biological product.

In some embodiments, the compartmenting peptide is oleosin, or a functional variant or fragment or orthologue thereof. In some embodiments, the compartmenting peptide comprises a hydrophobic region of oleosin, or a functional variant or orthologue thereof.

In some embodiments, the construct further comprises a coding sequence encoding a transit signal peptide to control the location of the droplet body formation.

In some embodiments, the location of the droplet body formation is the organelle where the targeted biological product is synthesised.

In some embodiments, the transit signal peptide directs droplet body formation in the chloroplast.

In some embodiments, the construct further comprises a coding sequence encoding an enhancing protein which enhances the production of the targeted biological product.

In some embodiments, the enhancing protein is an enzyme involved in the synthetic pathway of the targeted biological product.

In some embodiments, the expressed enhancing protein is fused with a transit signal peptide which directs the location of the enhancing protein to the same location as the droplet body formation.

In some embodiments, the enhancing protein is two or more enzymes whose expression increases terpene production in a plant.

In some embodiments, the enhancing protein is a synthetic enzyme complex.

In some embodiments, the enhancing protein is farnesyl pyrophosphate synthase (FPPS), or squalene synthase (SQS), or both farnesyl pyrophosphate synthase (FPPS) and squalene synthase (SQS).

In some embodiments, the enhancing protein comprises squalene synthase (SQS) and one or more upstream enzymes involved in terpene biosynthesis.

In some embodiments, the upstream enzyme is selected from the group consisting of: farnesyl pyrophosphate synthase (FPPS), geranyl diphosphate synthase (GPPS) and geranylgeranyl diphosphate synthase (GGPPS).

In some embodiments, the construct further comprises a coding sequence encoding a protein to form a complex comprising the squalene synthase and the one or more enzymes.

In some embodiments, the complex forming protein is scaffoldin.

In some embodiments, the construct further comprises a coding sequence encoding a substrate channeling protein which enhances the production of the targeted biological product by promoting substrate channeling within the metabolic pathway leading to synthesis of the product.

In some embodiments, the substrate channeling protein is scaffoldin.

In some embodiments, the substrate channeling is achieved by providing enzymes in close physical proximity to one another.

In some embodiments, the enzymes are bound to one another.

In some embodiments, the construct encodes a protein complex which is configured to couple with the compartmenting peptide.

In some embodiments, the protein complex comprises one or more proteins selected from the group consisting of: an enhancing protein and a substrate channeling protein.

According to a second aspect of the invention, a recombinant vector is provided, comprising the genetic construct of the first aspect.

According to a third aspect, there is provided a method of increasing the yield of a biological product in a plant compared to the yield of the biological product in a wild-type plant cultured under the same conditions, the method comprising transforming a plant cell with the genetic construct of the first aspect, or the vector of the second aspect, and regenerating a plant from the transformed cell.

In some embodiments, the biological product is a biofuel or a biofuel intermediate.

In some embodiments, the biological product is a therapeutic compound, such as a nutraceutical compound or a terpenoid or a terpenoid-derived compound.

In some embodiments, the biological product is a bioplastic, such as one selected from the group consisting of PHA, PHB, and PLA.

In some embodiments, the biological product is a terpene.

According to a fourth aspect of the invention, there is provided a method of producing a transgenic plant which produces a yield of a biological product which is higher than that of a corresponding wild-type plant cultured under the same conditions, the method comprising transforming a plant cell with the genetic construct of the first aspect or the vector of the second aspect, and regenerating a plant from the transformed cell.

In some embodiments, the plant is a monocotyledonous plant, such as one selected from the group consisting of *Oryza, Arundo, Hordeum*, and *Triticum*.

In some embodiments, the plant is a dicotyledonous plant, such as one selected from the group consisting of *Arabidopsis, Nicotiana, Lycopersicon, Glycine, Brassica, Vitis, Solanum, Manihot, Arachis, Malus, Citrus, Gossypium, Lactuca*, and *Raphanus*.

According to a fifth aspect of the invention, a transgenic plant is provided comprising the genetic construct of the first aspect or the vector of the second.

According to a sixth aspect of the invention, there is provided use of an exogenous nucleic acid sequence encoding a peptide for increasing the yield in a plant of a biological product by transformation of the plant with the exogenous nucleic acid sequence, wherein expression of the peptide leads to formation of a droplet body comprising the biological product.

In some embodiments of the use, the peptide comprises oleosin, or a functional variant or fragment or an orthologue thereof.

According to a seventh aspect of the invention, a host cell is provided comprising the genetic construct of the first aspect or the vector of the second aspect.

According to an eighth aspect of the invention, a plant propagation product is provided, the product being obtainable from the transgenic plant of the fifth aspect.

According to a ninth aspect of the invention, a biological product is provided, the product being obtained from a modified plant comprising the genetic construct of the first aspect or the vector of the second aspect.

In some embodiments, the biological product is a biofuel or a biofuel intermediate.

In some embodiments, the biological product is a therapeutic compound, such as a nutraceutical compound or a terpenoid or terpenoid-derived compound.

In some embodiments, the biological product is a bioplastic.

In some embodiments, the biological product is a terpene.

According to a tenth aspect of the invention, there is provided a plant part containing higher levels of a biological product than a corresponding part of a wild-type plant cultured under the same conditions, wherein the plant part is harvested from the transgenic plant of the fifth aspect or produced by the method of the third or fourth aspect.

In some embodiments, the plant part is the leaf.

BRIEF DESCRIPTION OF THE FIGURES

In order that aspects of the invention may be more fully understood, embodiments thereof are described, by way of illustrative example, with reference to the accompanying drawing in which:

FIG. 6A shows the amino acid sequence of *Arabidopsis thaliana* Oleosin (AtOLE) (SEQ ID NO: 9). FIG. 6B shows the different regions of this sequence, with the amino acid sequence of the hydrophobic region of AtOLE set out (SEQ ID NO: 10). FIG. 6C shows two genetic constructs for expression of a hydrophobic protein for compartmentation of a biological product such as a terpene.

FIG. 7A shows the imaging of the expression product of a genetic construct comprising the full oleosin sequence (AtOLE) together with green fluorescence protein (GFP). FIG. 7B shows the imaging of the expression product of a genetic construct comprising the HPT (designed hydrophobic protein), which is derived from the hydrophobic region of the AtOLE together with green fluorescence protein (GFP). The imaging shows the HPT protein effectively increases the terpene storage compared to the full AtOLE protein.

FIG. 10A shows the increased squalene yield in HPG-FPS-SQS lines as compared to the FPS-SQS lines in T1 generation of transgenic plants. FIG. 10B shows the plant height in T1 generation plants, whilst FIG. 10C shows the plant height in T2 generation plants.

DETAILED DESCRIPTION

Figure 1:
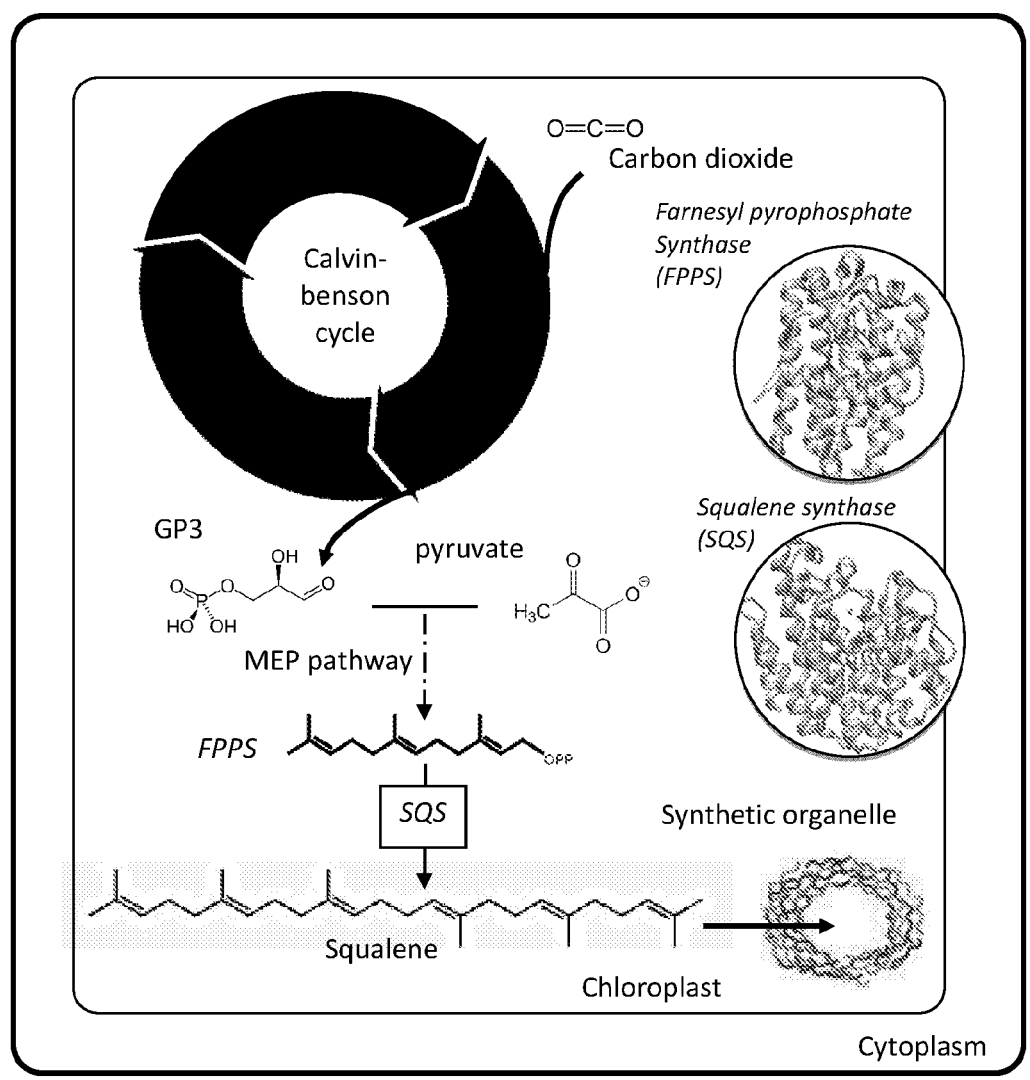
FIG. 1 shows the principle of compartmentation of storage and biosynthesis, where squalene biosynthesis and the synthetic organelle will be both engineered in chloroplast.

Many target biological products (also referred to herein as bioproducts) are compounds that can be used as pharmaceuticals, nutraceuticals, chemicals, and biofuel, but they are expensive due to their limited natural sources and complex chemical synthesis process. The present invention enables high levels of bioproducts to be accumulated in plants, thus reducing the cost of producing them. The present invention also provides a renewable and sustainable way to produce many of these compounds.

Terpenes are synthesized from a five-carbon precursor, isopentenyl diphosphate (IPP). Terpenoids, sometimes called isoprenoids, are a large and diverse class of naturally occurring organic chemicals similar to terpenes, derived from five-carbon isoprene units. Since terpenoids are the largest known class of natural products, many biochemical functions can be derived from them. Terpenoids may, for example, be useful as pharmaceuticals, chemicals, fragrances & flavorings, pesticides & crop production products, and biofuels. Pharmaceutical use may, for example, involve uses such as antiseptics, expectorants and diuretics, spasmolytics, sedatives, and the like.

In nature, terpenes and terpenoids have a broad variety of functions ranging from defense signals to plant growth hormone precursors. The diverse chemical structure and properties of these compounds enable broad application of terpenes and terpenoids as medicines, antioxidants, specialty chemicals and biofuels. Due to the importance of such applications, increasing terpene and/or terpenoid production in plants and microbes has been extensively studied, in particular, with regard to the optimization of up-stream biosynthesis pathways and the terpene synthase for target compound production.

Several inherent challenges have limited the further increase of terpene yield in planta. First, terpene biosynthesis is subject to extensive regulations in planta, where end product and intermediates often feedback to inactivate the key enzymes, down-regulate the pathway gene expression, and even impact the cell growth and physiology. In higher plants, the terpene precursors are produced in two pathways: the cytosol MVA (mevalonate) pathway and the chloroplast MEP (2-C-methyl-D-erythritol 4-phosphate) pathway starting from G3P (glyceraldehyde-3-phosphate) and pyruvate. Taken the plastid MEP pathway as an example, the terpene biosynthesis intermediates IPP (isopentenyl diphosphate) and DMAPP (dimethylallyl diphosphate) can bind and inactivate the committed step enzyme DXPS (1-deoxy-D-xylulose-5-phosphate synthase). Second, many valuable terpene compounds can be modified by downstream reactions and thus do not accumulate at a high level. For example, squalene is a triterpene broadly used in cosmetic and pharmaceutical industries, yet the production of the compound in cyanobacteria and yeast are often hampered by downstream enzymes like squalene hopene cyclase. Third, the accumulation of some terpene compounds can be toxic to the cells and terpene products are thus often conjugated with sugar, secreted, or modified in the cells, which posted a challenge in accumulating a target compound.

Various strategies have been developed to address these challenges including knocking down the downstream genes, compartment the production, and balancing the enzymes in the pathway. Not all of these strategies can be readily implemented in higher plants due to the much more complicated genetic modification in planta as compared to that in microorganisms. In higher plants, the accumulation of higher level of terpene are particularly challenging due to the more extensive biosynthesis pathway regulations and downstream modification. Despite the challenges, the precedent for large scale accumulation of terpenes exists. In particular, triterpenes have been shown to accumulate up to 75% of the dry weight of the green microalga *Botryococcus braunii*. Terpenoids can be stored in special plant structures including glandular trichomes, sheath cells, and vascular tissues. However, enhancing terpene production by over-expressing FPS and SQS in trichome led to mosaic and dwarf phenotype. Considering all these challenges, we hereby developed a new strategy to compartment the terpene biosynthesis and storage to achieve a record yield of squalene in planta without detrimental effects on growth and carbon assimilation. The strategy well addressed the aforementioned challenges by storing the target terpene compound in a synthetic organelle to alleviate the pathway feedback and avoid toxicity and downstream modification.

The principle of the present invention is shown in FIG. 1, where a chloroplast-generated droplet was designed by introducing a synthetic hydrophobic protein (HP) derived from oleosin. Previous studies established that over-expressing oleosin protein can enhance lipid droplet formation and thus increase lipid accumulation in plant seeds and leaves. However, no study has shown that high value terpene accumulation can be enhanced by introducing lipid droplet. In fact, the strategies for enhancing lipid yield cannot be readily applicable to terpene accumulation, in that the target compound biosynthesis needs to be co-located with droplet organelle. In plants, oleosin is generally targeted to ER, where the TAG is produced and lipid droplet is formed. A successful design would require the co-localization of terpene biosynthesis and droplet formation for storage of hydrophobic terpene. It has been established that targeted over-expressing the FPPS (farnesyl pyrophosphate synthase) and SQS (squalene synthase) in chloroplast led to the production of squalene at 600 ug/G FW (microgram per gram of fresh weight) without detrimental effects on growth and development. We the invention provides a new strategy to compartment both squalene storage and biosynthesis in chloroplast to enhance the production of this high value compound with broad applications.

Terpene and terpenoid storage in plants is a particularly important area of investigation. Oil or lipid bodies are storage "compartments" within a plant cell that comprise a neutral lipid core of triacylglycerols (TAG) and sterol esters (SE). Oleosin is a structural protein which is involved in biosynthesis and mobilization of plant oil bodies. In higher plants, oleosin is generally produced from the endoplasmic reticulum (ER), and not from the chloroplast. This means that such oil bodies are able to compartment products synthesized in the ER. However, the formation of such oleosin-based oil or lipid bodies cannot be coupled with the compartmentation production from the chloroplast. The present invention has enabled the formation of a droplet generated from chloroplast, thereby allowing the product of a synthetic pathway of the chloroplast to be compartmented.

The present invention provides a method for increasing the yield of a biological product. In some embodiments, this is achieved by reducing feedback in the pathway by compartmentation of the end product. In some embodiments, the increased yield is achieved by efficient substrate channeling of product intermediates. This involves the passing of the intermediary product of one enzyme directly to another enzyme or active site. Such channeling leads to more rapid and efficient metabolic pathways.

In some embodiments, the present invention provides a method of producing a biological product in a plant and storing it efficiently in the cell. In some embodiments, this method comprises expressing in the plant a uniquely designed hydrophobic protein. The technology compartments biological products produced in plants. In some embodiments, the invention relates to directing expression of a protein to form a droplet body from a plastid where the desired biological product is synthesized. For example, where the desired biological product is a terpene compound produced in chloroplasts, the invention involves a genetic construct which engineers a chloroplast-originated droplet body to store the biological product. Moreover, the invention may remove the substrate inhibition at both intermediate and end product levels, thereby allowing a higher yield of the biological product.

In some embodiments of the present invention, a droplet body is formed to compartment the biological product or a product intermediate. In some embodiments, the droplet body originates from the chloroplast and will therefore be suited to compartmenting a biological product formed in the plant's chloroplast. However, in other embodiments, the peptide forming the droplet body coating may include a signal which locates the peptide, and therefore the droplet body, in a different part of the plant cell, for example in a different cell organelle, so that it is suitable for compartmenting products produced in those other parts of the plant cell. In some embodiments, the peptide forming the droplet body may be designed to ensure that the droplet bodies are formed in parts of the plant where such bodies are not usually located, and/or in plants where such bodies are not normally produced.

As used herein, a "compartmenting peptide" is a peptide, polypeptide or protein which is capable of forming a coating around a lipid or terpene droplet to form a droplet body. Such droplet bodies can be capable of compartmenting biological products or biological product intermediates. In some embodiments, the droplet body comprises a lipid or oil droplet which is surrounded by a peptide which forms a coating or barrier around the lipid or oil to form a stable body. The surrounding peptide is the compartmenting peptide.

In some embodiments, the compartmenting peptide is an oleosin. Oleosins are proteins of 16 kDa to 24 kDa and are composed of three domains: an N-terminal hydrophilic region of variable length (from 30 to 60 residues); a central hydrophobic domain of about 70 residues and a C-terminal amphipathic region of variable length (from 60 to 100 residues). Oleosins are structural proteins found in vascular plant oil bodies in which oleosins form a coating which surrounds oil or lipid droplets comprising triacylglyceride (TAG). Models show the hydrophobic region of oleosins forming a hairpin-like shape that is inserted inside the triacylglyceride (TAG), while the hydrophilic parts are left outside oil bodies. Oleosins are generally produced in the endoplasmic reticulum and the lipid or oil bodies that they form a structural part of bud off the endoplasmic reticulum.

In some embodiments of the invention, the compartmenting peptide is a protein, polypeptide or peptide that can be derived from or based on an oleosin, including, for example, a functional variant, fragment, orthologue or variant of oleosin. In some embodiments, the compartmenting peptide is one which forms the coating of a droplet body, including, for example an oil or lipid body.

In some embodiments, the compartmenting peptide has a hydrophobic domain.

In some embodiments, the compartmenting peptide includes a signal which determines the location of the compartmenting peptide and of the droplet body comprising the peptide in the plant and/or in individual cells.

In some embodiments, a compartmenting peptide is used in plants to create a chloroplast-originated oil body in which a biological product can be stored. In some embodiments, the biological product is chloroplast-derived. In some embodiments, the biological product is one or more terpene compounds. In some embodiments, the compartmenting peptide forms a droplet body by surrounding a terpene droplet. In other embodiments, the compartmenting peptide forms a droplet body by surrounding an oil or lipid droplet and a biological product.

In nature, oleosins are generally produced by the endoplasmic reticulum, and droplets that they form generally contain lipid. There has been no previous study showing that one can control the location where an oleosin-based lipid droplet is formed. Furthermore, there have been no previous studies showing that one can control the droplet to store a different, targeted biological product, such as a terpene compound. There are reports that chloroplast-originated oil bodies may occur naturally in plants. However, they exist only in certain parts of plants, such as carrot root. No one has previously shown how to engineer the production of a droplet body from chloroplasts in leaf, stem and other tissues.

The capacity to direct production of a droplet body in different tissues expands the type of terpene, terpene derivatives and other biological products that the droplet bodies can store. By bringing the location of terpene synthesis and droplet formation together, either through protein complex design or compartmentation, the inventors were able to realize the storage of a terpene compound. In addition, by innovative design of protein, the inventors were able to achieve the origination of a droplet body from the chloroplast. The same strategy can be expanded to other organelles for controlled production and in planta storage of different compounds synthesized in said organelles.

Figure 5:
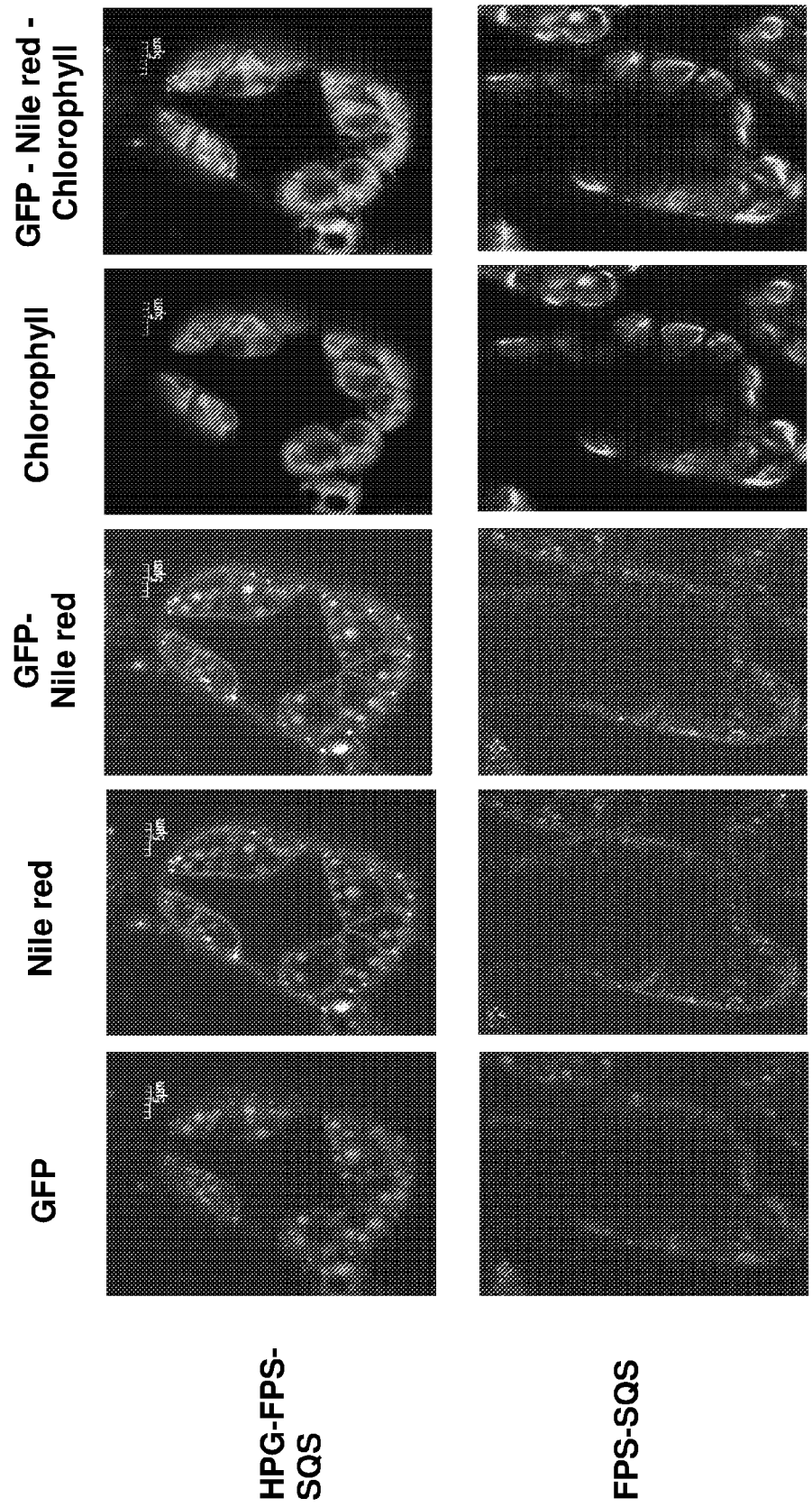
FIG. 5 shows the confocal microscopy analysis of droplet formation in HPG-FPS-SQS lines as compared to the FPS-SQS lines.
Figure 6:
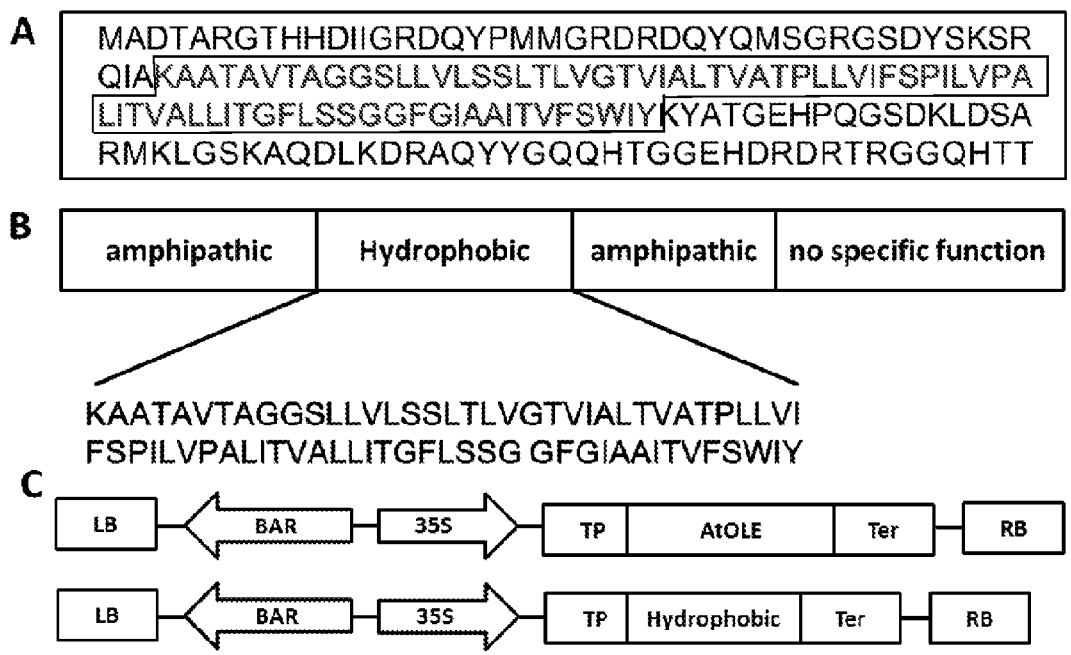
FIG. 6 shows the design of hydrophobic protein (HP) and hydrophobic protein in combination with GFP (HPG).
Figure 7:
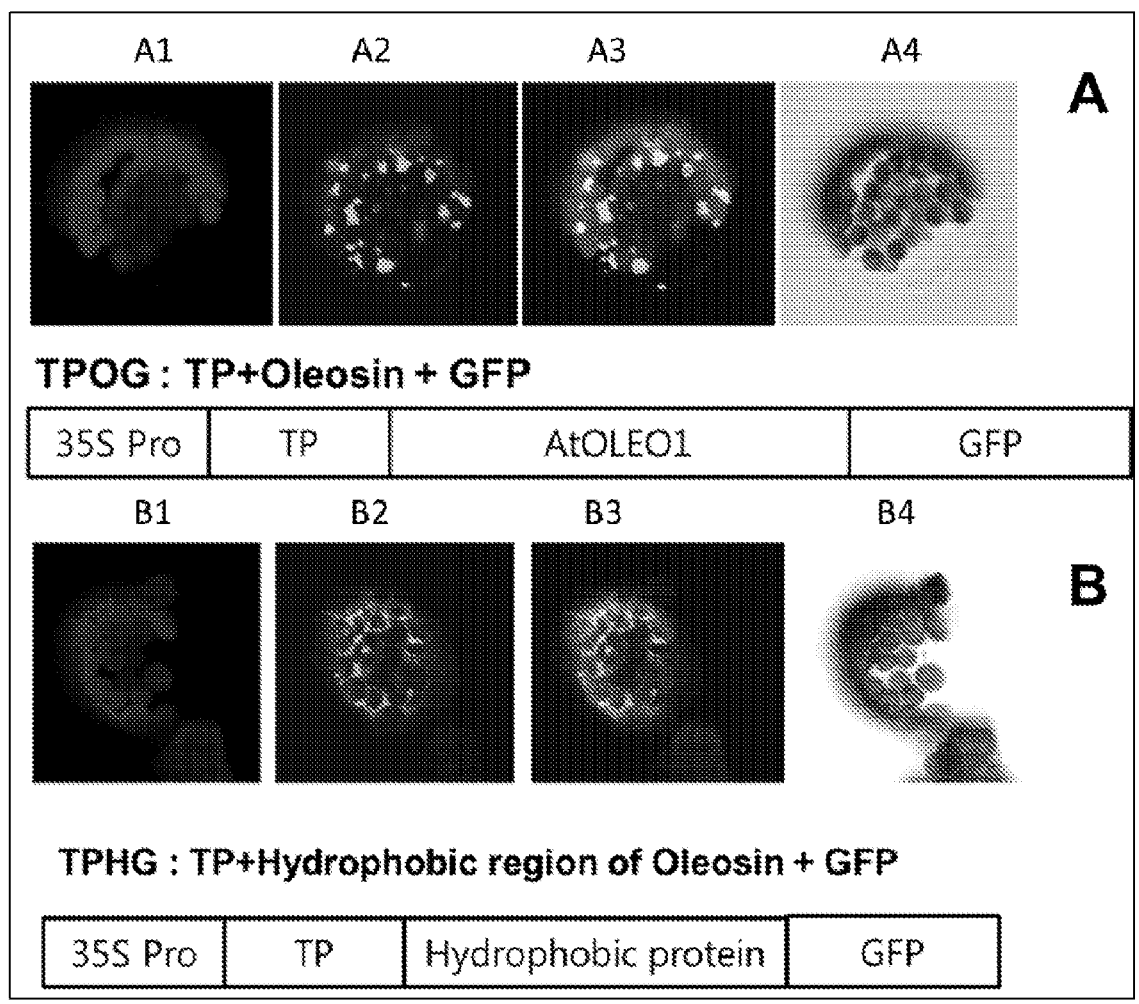
FIG. 7 shows confocal microscopy analysis of transiently expressed oleosin and hydrophobic protein in protoplast.

Different designed proteins derived from *Arabidopsis* oleosin were screened using agroinfiltration for transient expression. These proteins included: original oleosin; oleosin with plastid transit peptide and GFP (TOG); and a hydrophobic protein (HPG) derived from oleosin by removing the branching hydrophilic domain of the protein and adding a chloroplast transit peptide along with GFP (FIG. 6). As shown in FIG. 7, the HPG protein signal seemed to locate on the chloroplast membrane. The HPG protein and HP protein (HPG without GFP) were then integrated with chloroplast located FPPS and SQS and transformed into tobacco to compartment the terpene storage and synthesis. In order to evaluate the formation of synthetic droplet in chloroplast, confocal microscopy was carried out to analyze the GFP, Nile red staining and chloroplast auto-fluorescence. Nile red staining can be used to visualize the accumulation of neutral lipid or hydrophobic hydrocarbon like squalene. As shown in FIG. 5, the Nile red stained droplet structure could be clearly visualized in the HPG transformed tobacco. The GFP signal from HPG transformed plants overlapped with the Nile red fluorescence, indicating that the HPG protein has promoted the formation of droplet containing neutral lipid and/or squalene. In addition, the further overlapping with auto-fluorescence from chlorophyll indicated that the synthetic droplet organelle located in or near the chloroplast. Overall, HPG protein can be transit to the chloroplast and promote the formation of a new synthetic organelle in chloroplast to store neutral lipid or hydrocarbon.

In some embodiments, the compartmenting peptide is designed to have beneficial properties for use in the present invention. In some embodiments, the compartmenting peptides enable droplet body formation in plants, wherein the droplet body contains the targeted biological product, for example a terpene compound.

In some embodiments, the construct for transformation into plants include the following components: a promoter (for example, a constitutive promoter such as cauliflower mosaic virus 35S promoter), a transit peptide (for example, from rubisco small subunit, the first 58 amino acid), a hydrophobic protein with two transmembrane domains and a hairpin loop, and a terminator (for example, Tnos).

In some embodiments, including those illustrated by the examples described below, the compartmenting peptide may be based upon or derived from the oleosin from *Arabidopsis*. By removing the signal peptide and the hydrophilic regions as well as adding additional signal peptides, it was possible to change the location of the oleosin and target it to where biosynthesis of the targeted biological product take place. Furthermore, it was possible to remove the topology control of the droplet forming protein to form the droplet bodies from the chloroplast and to bud out from the chloroplast. A similar effect could be achieved by engineering various lipid droplet or other droplet formation proteins using the same principle. These other droplet formation proteins may be based upon or derived from other naturally-occurring proteins, or they could be hydrophobic proteins that have droplet forming properties which allow them to be useful in this manner to compartment a desired biological product. It is considered that a hydrophobic region of the proteins is required in order to form the structural coating surrounding a lipid or oil droplet, or around a terpene droplet, in order to form a droplet body as used in the present invention.

The genetic constructs of the present invention include several components. Basically, the constructs contain a combination of a promoter to start gene expression, a transit peptide for targeted expression, a compartmenting peptide such as a hydrophobic protein to form the droplet, and terminator to stop gene expression. Multiple choices for each component can be used. For example, in some embodiments, the promoter may be a constitutive promoter. In other embodiments, the promoter may be a tissue-specific or otherwise controlled promoter. The core innovation lies in the use of a compartmenting peptide and combining the location of the compartmenting peptide with the location of production of the target biological compound.

First, the genetic construct comprises a promoter. In some embodiments, the promoter is a constitutive promoter. One particular example of a constitutive promoter that may be included in the construct is the 35S promoter. The promoter may be used to drive the expression of the compartmenting peptide. However, other known promoters which are suitable for driving a high level of protein expression can be used.

Second, the genetic construct may comprise transit peptide. In some embodiments, the transit peptide is chosen for the desired organelle, which is where the production of the targeted biological product is located and/or where droplet body formation is desired. For example, the construct may comprise a transit peptide derived from the small subunit of potato rubisco, which targets the chloroplast. Similar transit peptides can also be derived from different plant species and different genes which target the desired organelle in the plant, such as, for example, the chloroplast.

Third, the genetic construct may comprise a coding sequence encoding a compartmenting peptide. In some embodiments, this coding sequence may encode a hydrophobic protein. In some embodiments, the hydrophobic protein may be an oleosin or at least a hydrophobic region of an oleosin. As aforementioned, various hydrophobic proteins can be used as compartmenting peptides for the formation of droplet bodies. In at least some embodiments, the compartmenting peptide comprises a hydrophobic protein with two transmembrane domains and a hydrophilic hairpin loop. A peptide with these regions will fold and act in a manner similar to an oleosin, with multiple peptides forming an outer layer surrounding a droplet of oil or lipid, or a droplet of terpene, to form a droplet body. In some embodiments, the compartmenting peptide is similar to an oleosin protein, but has been modified, for example, to control the location of expression. In some embodiments, the modification of the oleosin involves, for example, removal of the transit peptides and/or side chain from the oleosin.

Fourth, the genetic construct may comprise a terminator sequence. Any known terminator series can be used to terminate the gene expression here.

In order to show the efficacy of the present invention, two genetic constructs were constructed, one encoding a full length oleosin, the other encoding the hydrophobic part of oleo sin (see FIG. 6). The constructs comprise a promoter of 35S promoters, a Chloroplast signal peptide, and Tnos for ending transcription.

The results of virus-based transient expression of the constructs of FIG. 6 in tobacco leaf are shown in FIG. 7. The results indicate that the constructs allow oleosin or an oleosin-derived hydrophobic protein to form droplet bodies in the chloroplast and cytosol. In particular, by fusing a chloroplast signal to the oleosin or oleosin-derived hydrophobic protein (which comprises two hydrophobic domains which are aligned and are joined by a loop) chloroplast originated droplet formation may be achieved.

In some embodiments of the invention, an alternative to virus-based, transient expression is stable transformation.

The controlled formation of droplet bodies according to the invention can allow the compartmenting of a targeted biological product. For example, it may enhance storage of terpenes or terpenoids in a plant. The invention aims to increase terpene or terpenoid storage by promoting the formation of terpene or terpenoid droplets to reduce the cell toxicity and product inhibition. The present invention thus represents an improvement over the art by providing a method of producing a bioproduct in a plant by introducing into the plant a bacterial gene that will compartment the bioproduct and/or its intermediates. In some embodiments, the present invention further enables the plant to produce greater amounts of the bioproduct.

In some embodiments, the invention further relates to measures to enhance the production of the desired biological product in a plant. In some embodiments, increased production is achieved by introducing into the plant the enzymes for targeted pathways. For example, the phaABC operon can be introduced into plants to promote the production of bioplastics like PHA and PHB. In the same way, the various genes involved in Astaxanthin production can be increased to improve the level of production. Traditionally, the overexpression of targeted genes in certain pathways is the typical way to improve yield of target products. In the present invention, new approaches are provided to improve bioproduction yield. These include: combining the production pathway with targeted organelle to store target compound; forming a protein complex to remove intermediate; and combining the protein complex, pathway compartmentation, and targeted organelle design to achieve the storage of target compound efficiently. These methods have been demonstrated to effectively improve terpene yield.

In some embodiments, a synthetic enzyme complex is provided to increase terpene production and yield, and to reduce the intermediate inhibition of the reaction. The complex enzyme removes the key intermediates in the pathway to increase terpene production. Pathway intermediate and end products often inhibit the enzymes in the upstream pathway for biosynthesis. This is a common phenomenon that can be addressed by the present invention. Specifically, for terpene biosynthesis, intermediates isopentenyl diphosphate (IPP) and dimethylallyl diphosphate (DMAPP) inhibit the first enzyme of 2-C-methyl-d-erythritol-4-phosphate (MEP) pathway for upstream terpene biosynthesis, 1-deoxyxylulose 5-phosphate synthase (DXPS). In addition, intermediate farnesyl pyrophosphate (FPP) also inhibits upstream pathway components as indicated by previous research. The combination of farnesyl pyrophosphate synthase (FPPS) and squalene synthase (SQS) in a protein complex will effectively remove the pathway intermediate to enable a higher terpene production level. Such synergy is important for both improve the enzyme product yield and removal of pathway inhibition. The synergy comes from two effects. Firstly, the product from a first enzyme can be made immediately available to a second enzyme in an enzymatic pathway. This is called substrate channeling. The effect is the increased local concentration of the substrate for the second enzyme, thereby increasing the rate of the catalytic reaction. Secondly, the efficient utilization of the product from the first enzyme also removes the inhibitory effects of the product from the first enzyme for the entire pathway, which further improves the production.

Many terpenes and derived products such as squalene and astaxanthin are important for the nutraceutical and pharmaceutical industries. The production of these secondary metabolite compounds are often toxic to the cell or lead to feedback reactions to reduce the yield. In order to increase the yield, the aforementioned embodiments may be used to remove the intermediate product inhibition, enhance the flux to final terpene product, and increase the terpene product storage. The technology involves putting two important enzymes in terpene production into a complex. In particular, the last two enzymes for terpene production, as demonstrated by FPPS and SQS, are combined.

In some embodiments, the invention further comprises the use of a protein complex to achieve substrate channeling to enhance the yield of the biological product, such as terpene. The effective channeling of carbon and reducing equivalent using nano-machinery of multiple biocatalysts can be an effective approach to increase terpene yield both in vitro and in vivo. According to one embodiment, a synthetic two-enzyme complex containing farnesyl pyrophosphate synthase (FPPS) and squalene synthase (SQS) was constructed both in vitro and in vivo. In vitro results indicate the synthetic metabolons exhibited several-fold enhancement in reaction rates compared to non-complexed enzyme mixtures and such substrate synergy strongly depends on enzyme loading, substrate concentration and even ionic strength.

Figure 8:
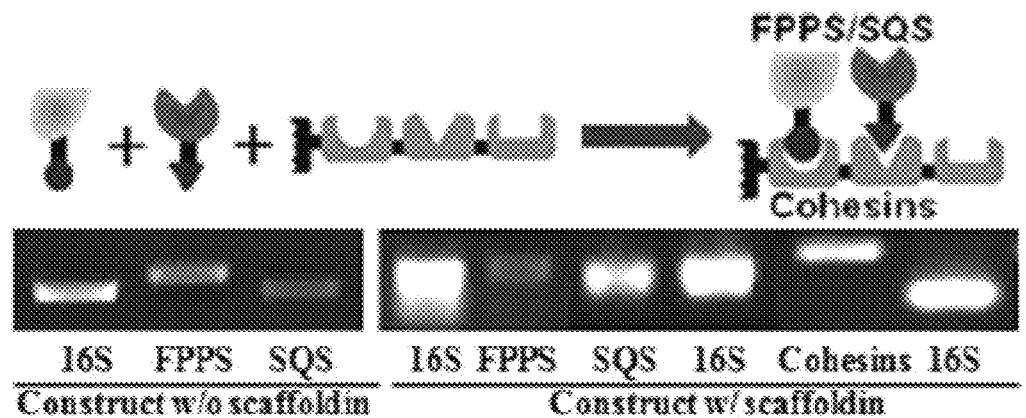
FIG. 8 shows the increase of terpene level resulting from the expression of a synthetic enzyme complex designed to remove the intermediate effects. The level of terpene and terpene derivatives increased significantly.
Figure 8:
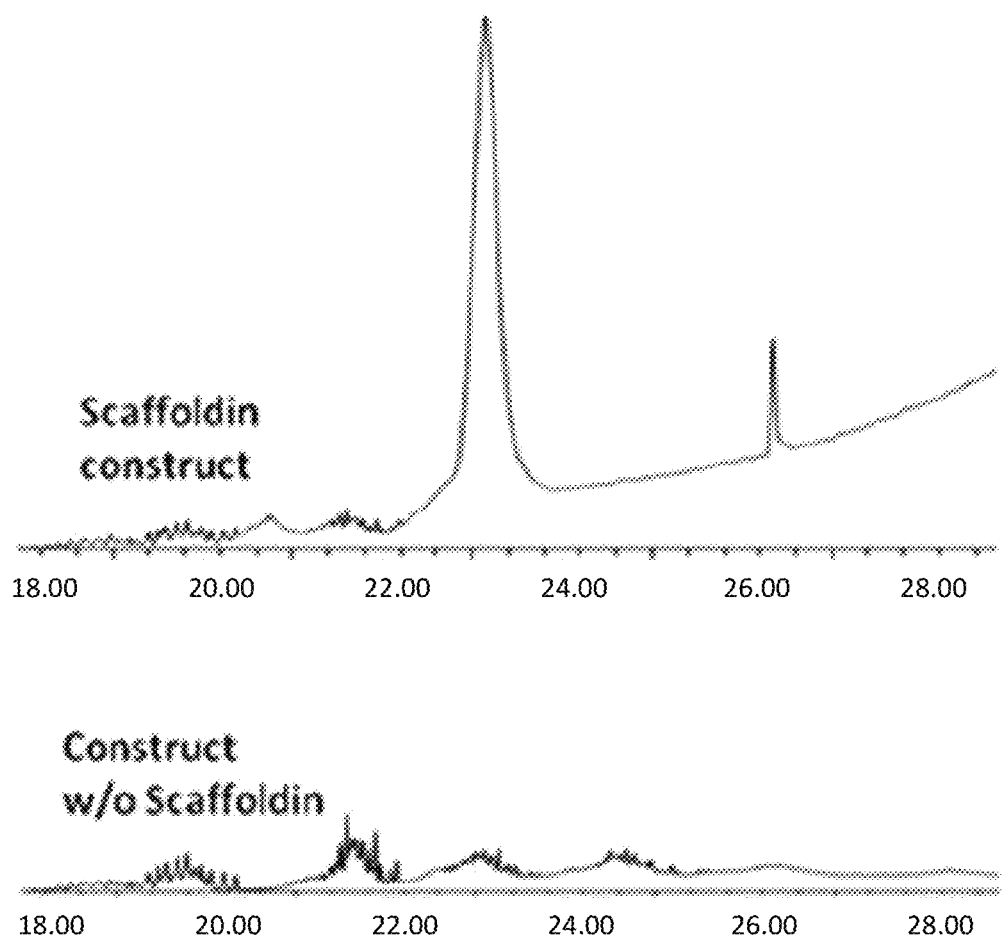

As shown in FIG. 8, the implementation of this complex in cyanobacteria has led to a significant increase in terpene production. This is a demonstration of in vivo production level increases. Basically, the major peak represents squalene and its derivative. As shown in the figure, in the complex design, the squalene production was significantly increased. The construct comprising scaffoldin led to significantly higher squalene yields than the construct without scaffoldin. The results highlight that the metabolon can be used to channel substrate to mitigate metabolic bottlenecks. In the specific example used to illustrate this aspect of the invention, the presence of the scaffoldin leads to an enzyme complex which is capable of substrate channeling to significantly enhance the efficiency of the metabolic pathway and yield of the biological product, in this case squalene.

The present invention represents a straightforward yet powerful solution to enable economically viable plant bioproducts production. This design is effective in terpene biosynthesis due to two reasons. First the first enzyme directly passes the product to the second enzyme as reactant, which increases the local concentration of the substrate. Second, the design removes the intermediate that could be toxic or inhibitory. The design can be implemented and has been proven to be implemented in many pathways. We can use it for bioplastics production. The key innovation will be combination of this design with the droplet design to achieve the storage of high concentrations of biological products, such as terpenes (see FIGS. 8 and 9).

In some embodiments, the aforementioned measures are combined to increase the yield of the biological product. More specifically, the formation of a droplet body, for example an oil or lipid body, suitable to capture the biological product or the product intermediate may be combined with an increase in the level of production of the biological product. Such a combination takes advantage of increased product yield as a result of both compartmenting the product or intermediates by droplet bodies and increased production. More importantly, the combination of measures allows the targeted compounds to be directly channeled into a designed droplet body. The combination of the two parts of the technology provides a synergistic effect. Basically, it will allow the production and storage to be coupled together. The production will be at the storage site and will thus achieve two effects. First, the storage efficiency will be higher. Second, the product will be removed to prevent the inhibitory effects.

This approach has the potential to enhance the production of a variety of plant bioproducts like terpenes (including squalene, leutin, astaxanthin, and others), terpenoids, polyhydroxyalkanoates (PHA), poly(hydroxybutyrate) (PHB), poly(lactic acid) (PLA), lipids, and others. The present invention dramatically decreases the bioproduct production costs for plants and can assist in the production of an economically viable biofuel, pharmaceuticals and chemicals. The present invention also provides a solution to increase the photosynthesis efficiency and biomass of C3 (carbon fixation) plants.

The term "bioproduct" as used herein refers to a product produced as a result of a biological process, such as terpene biosynthesis, or from a biological material, such as plants or plant parts. Many bioproducts have important commercial value. For example, β-caryophyllene, a major component of *Copaifera* oleoresin, can be directly used as a diesel fuel. In addition, artemisinin is an antimalarial drug isolated from *Artemisia annua* L. Squalene recently has been shown to be an important nutraceutical and can be widely used as vaccine carrier. Carotenoids such as lycopene, β-carotene, and astaxanthin are used as food colorants, animal feed supplements, and for nutritional and cosmetic purposes. More recently, carotenoids have received attention for their significant antioxidant activities and for their roles in inhibiting the onset of chronic diseases. PHA, PHB and PLA are promising bioplastics. Supply of these useful compounds from natural sources is limiting and expensive, and the cost of their total synthesis is prohibitive, and thus novel methods for their production are needed.

Terpenes, also referred to as terpenoids, are the largest group of natural products. All terpenoids are synthesized from a five-carbon precursor, isopentenyl diphosphate (IPP). Based on the isoprene structure and the length of the carbon chain, terpenoids can be classified into monoterpenes (10-carbon), sesquiterpenes (15-carbon), diterpenes (20-carbon), triterpenes (30-carbon) and tetraterpenes (40-carbon). In higher plants, terpenoids are synthesized with either the chloroplastic non-mevalonate (MEP) pathway, or the cytosolic mevalonate (MEV) pathway.

There are several different ways to combine the aforementioned technologies to achieve maximized yield of the targeted biological product. In a first embodiment, as aforementioned, the compartmentation can be combined with targeted droplet formation, where the droplet is formed in the organelle or cell compartment where the biosynthesis pathway is located. The production of target products thus synergize with the storage of target compounds. In a second embodiment, the protein complex can be coupled with a droplet forming protein. In this way, the biosynthesis of a target compound, and in some embodiments the enhanced biosynthesis of a target compound, can be directly coupled with storage. In a yet further embodiment, the compartmentation of a pathway is provided, wherein the protein complex and the droplet can all be combined together to improve the biological product (such as terpene) yield. The strategies can be also combined in other ways and further integrated with other pathways to achieve the highest bioproduct yield.

In certain embodiments, a biological product is produced by the method of the present invention or the production of a biological product is increased. Thus, in some embodiments, the wild-type plant produces the desired biological product and the invention is used to produce a transformed plant in which the yield of the biological product is increased. This may be as a result of the biological product being compartmented, thanks to the expression of the compartmenting peptide which leads to the formation of droplet bodies in which the biological product may be stored. In other embodiments, the wild-type plant may not produce the biological product and its production may be a result of genes added to the plant by transformation. In some embodiments, the yield of the product is enhanced by the compartmenting thereof as a result of the expression of the compartmenting peptide.

In some embodiments, expression of the designed hydrophobic protein in the plant results in an elevated level of said biological product. Optionally, the hydrophobic protein is derived from or based on an oleosin.

In some embodiments, the plant may be a monocotyledonous plant such as *Oryza, Arundo, Hordeum,* or *Triticum,* or a dicotyledonous plant such as *Arabidopsis, Nicotiana, Lycopersicon, Glycine, Brassica, Vitis, Solanum, Manihot, Arachis, Malus, Citrus, Gossypium, Lactuca,* or *Raphanus.*

In some embodiments, the biological product may be a biofuel or a biofuel intermediate, a therapeutic compound such as a nutraceutical compound or a terpenoid-derived compound, a terpene compound with other application, a bioplastic such as one selected from the group consisting of PHA, PHB, and PLA, a terpene, or a carbon-containing product. In still further embodiments, the plant gene may be over-expressed, or the bacterial and plant genes may be expressed together.

In some embodiments, the present invention provides a method of producing a biological product from a plant, comprising coupling a protein complex for substrate channeling and a hydrophobic protein design for storage of compound. In some embodiments, the biological product may be a biofuel or a therapeutic compound.

DNA Molecules

As used herein, the term "DNA" or "DNA molecule" refers to a double-stranded DNA molecule of genomic or synthetic origin, i.e. a polymer of deoxyribonucleotide bases or a polynucleotide molecule, read from the 5' (upstream) end to the 3' (downstream) end. As used herein, the term "DNA sequence" refers to the nucleotide sequence of a DNA molecule. The nomenclature used herein corresponds to that of Title 37 of the United States Code of Federal Regulations § 1.822, and set forth in the tables in WIPO Standard ST.25 (1998), Appendix 2, Tables 1 and 3.

As used herein, the term "isolated DNA molecule" refers to a DNA molecule at least partially separated from other molecules normally associated with it in its native or natural state. In one embodiment, the term "isolated" refers to a DNA molecule that is at least partially separated from some of the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated when integrated into the chromosome of a host cell or present in a nucleic acid solution with other DNA molecules, in that they are not in their native state.

Any number of methods well known to those skilled in the art can be used to isolate and manipulate a DNA molecule, or fragment thereof, as disclosed in the present invention. For example, polymerase chain reaction (PCR) technology can be used to amplify a particular starting DNA molecule and/or to produce variants of the original molecule. DNA molecules, or fragments thereof, can also be obtained by other techniques, such as by directly synthesizing the fragment by chemical means, as is commonly practiced by using an automated oligonucleotide synthesizer.

Regulatory Elements

A regulatory element is a DNA molecule having gene regulatory activity, i.e. one that has the ability to affect the transcription and/or translation of an operably linked transcribable polynucleotide molecule. The term "gene regulatory activity" thus refers to the ability to affect the expression pattern of an operably linked transcribable polynucleotide molecule by affecting the transcription and/or translation of that operably linked transcribable polynucleotide molecule. As used herein, a transcriptional regulatory expression element group may be comprised of expression elements, such as enhancers, promoters, leaders, and introns, operably linked. Thus, a transcriptional regulatory expression element group may be comprised, for instance, of a promoter operably linked 5' to a leader sequence, which is in turn operably linked 5' to an intron sequence. The intron sequence may be comprised of a sequence beginning at the point of the first intron/exon splice junction of the native sequence and may be further comprised of a small leader fragment comprising the second intron/exon splice junction so as to provide for proper intron/exon processing to facilitate transcription and proper processing of the resulting transcript. Leaders and introns may positively affect transcription of an operably linked transcribable polynucleotide molecule as well as translation of the resulting transcribed RNA. The pre-processed RNA molecule comprises leaders and introns, which may affect the post-transcriptional processing of the transcribed RNA and/or the export of the transcribed RNA molecule from the cell nucleus into the cytoplasm. Following post-transcriptional processing of the transcribed RNA molecule, the leader sequence may be retained as part of the final messenger RNA and may positively affect the translation of the messenger RNA molecule.

Regulatory elements such as promoters, leaders, introns, and transcription termination regions are DNA molecules that have gene regulatory activity and play an integral part in the overall expression of genes in living cells. The term "regulatory element" refers to a DNA molecule having gene regulatory activity, i.e. one that has the ability to affect the transcription and/or translation of an operably linked transcribable polynucleotide molecule. Isolated regulatory elements, such as promoters and leaders, which function in plants are therefore useful for modifying plant phenotypes through the methods of genetic engineering.

Regulatory elements may be characterized by their expression pattern effects (qualitatively and/or quantitatively), e.g. positive or negative effects and/or constitutive or other effects, such as by their temporal, spatial, developmental, tissue, environmental, physiological, pathological, cell cycle, and/or chemically responsive expression pattern, and any combination thereof, as well as by quantitative or qualitative indications. A promoter may be useful as a regulatory element for modulating the expression of an operably linked transcribable polynucleotide molecule.

As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as an mRNA, a dsRNA, a tRNA, an rRNA, a miRNA, and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

As used herein, the term "promoter" refers generally to a DNA molecule that is involved in recognition and binding of RNA polymerase II and other proteins (trans-acting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, i.e. a promoter produced through the fusion of two or more heterologous DNA molecules. In specific embodiments of the invention, such molecules and any variants or derivatives thereof as described herein are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" that provides a basal level of transcription and is comprised of a TATA box or equivalent sequence for recognition and binding of the RNA polymerase II complex for initiation of transcription.

Compositions derived from a promoter useful for the present invention, such as internal or 5' deletions, for example, can be produced using methods known in the art to improve or alter expression, including by removing elements that have either positive or negative effects on expression; duplicating elements that have positive or negative effects on expression; and/or duplicating or removing elements that have tissue- or cell-specific effects on expression. Further deletions can be made to remove any elements that have positive or negative; tissue specific; cell specific; or timing specific (such as, but not limited to, circadian rhythms) effects on expression. The efficacy of the modifications, duplications or deletions described herein on the desired expression aspects of a particular transgene may be tested empirically in stable and transient plant assays, such as those described in the working examples herein, so as to validate the results, which may vary depending upon the changes made and the goal of the change in the starting molecule.

As used herein, the term "leader" refers to a DNA molecule isolated from the untranslated 5' region (5' UTR) of a genomic copy of a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable polynucleotide molecule. Leader molecules may be used with a heterologous promoter or with their native promoter. Promoter molecules of the present invention may thus be operably linked to their native leader or may be operably linked to a heterologous leader. In specific embodiments, such sequences may be provided defined as being capable of acting as a leader in a host cell, including, for example, a transgenic plant cell. In one embodiment, such sequences are decoded as comprising leader activity.

A leader sequence (5' UTR) in accordance with the present invention may be comprised of regulatory elements or may adopt secondary structures that can have an effect on transcription or translation of a transgene. Such a leader sequence may be used in accordance with the present invention to make chimeric regulatory elements that affect transcription or translation of a transgene. In addition, such a leader sequence may be used to make chimeric leader sequences that affect transcription or translation of a transgene.

The introduction of a foreign gene into a new plant host does not always result in high expression of the incoming gene. Furthermore, if dealing with complex traits, it is sometimes necessary to modulate several genes with spatially or temporally different expression pattern. Introns can principally provide such modulation. However, multiple uses of the same intron in one plant have been shown to exhibit disadvantages. In those cases, it is necessary to have a collection of basic control elements for the construction of appropriate recombinant DNA elements. The number of introns known in the art to have expression-enhancing properties is limited, and thus, alternatives are needed.

In accordance with the present invention, a promoter or promoter fragment may be analyzed for the presence of known promoter elements, i.e. DNA sequence characteristics, such as a TATA-box and other known transcription factor binding site motifs. Identification of such known promoter elements may be used by one of skill in the art to design variants of a promoter having a similar expression pattern to the original promoter.

As used herein, the term "enhancer" or "enhancer element" refers to a cis-acting transcriptional regulatory element (a cis-element), which confers an aspect of the overall expression pattern, but is usually insufficient alone to drive transcription of an operably linked polynucleotide sequence. Unlike promoters, enhancer elements do not usually include a transcription start site (TSS), or TATA box or equivalent sequence. A promoter may naturally comprise one or more enhancer elements that affect the transcription of an operably linked polynucleotide sequence. An isolated enhancer element may also be fused to a promoter to produce a chimeric promoter cis-element, which confers an aspect of the overall modulation of gene expression. A promoter or promoter fragment may comprise one or more enhancer elements that affect the transcription of operably linked genes. Many promoter enhancer elements are believed to bind DNA-binding proteins and/or affect DNA topology, producing local conformations that selectively allow or restrict access of RNA polymerase to the DNA template, or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e. deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed by the present invention.

In plants, the inclusion of some introns in gene constructs leads to increased mRNA and protein accumulation relative to constructs lacking the intron. This effect has been termed "intron mediated enhancement" (IME) of gene expression (Mascarenhas et al., (1990) *Plant Mol. Biol.* 15:913-920). Introns known to stimulate expression in plants have been identified in maize genes [e.g., tubA1, Adh1, Sh1, Ubi1 (Jeon et al., *Plant Physiol.* 123:1005-1014, 2000; Callis et al., *Genes Dev.* 1:1183-1200, 1987; Vasil et al., *Plant Physiol.* 91:1575-1579, 1989; Christiansen et al., *Plant Mol. Biol.* 18:675-689, 1992) and in rice genes (e.g., salt, tpi: McElroy et al., *Plant Cell* 2:163-171, 1990; Xu et al., *Plant Physiol.* 106:459-467, 1994). Similarly, introns from dicotyledonous plant genes such as *petunia* (e.g., rbcS), potato (e.g., st-ls1) and *Arabidopsis thaliana* (e.g., ubq3 and pati) have been found to elevate gene expression rates (Dean et al., *Plant Cell* 1:201-208, 1989; Leon et al., *Plant Physiol.* 95:968-972, 1991; Norris et al., *Plant Mol Biol.* 21:895-906, 1993; Rose and Last, *Plant J.* 11:455-464, 1997). It has been shown that deletions or mutations within the splice sites of an intron reduce gene expression, indicating that splicing might be needed for IME (Mascarenhas et al., *Plant Mol Biol.* 15:913-920, 1990; Clancy and Hannah, *Plant Physiol.* 130:918-929, 2002). However, such splicing is not required for a certain IME in dicotyledonous plants, as shown by point mutations within the splice sites of the pati gene from *A. thaliana* (Rose and Beliakoff, *Plant Physiol.* 122:535-542, 2000).

Enhancement of gene expression by introns is not a general phenomenon because some intron insertions into recombinant expression cassettes fail to enhance expression (e.g., introns from dicot genes such as the rbcS gene from pea, the phaseolin gene from bean, and the stls-1 gene from *Solanum tuberosum*) and introns from maize genes (the ninth intron of the adh1 gene, and the first intron of the hsp81 gene) (Chee et al., *Gene* 41:47-57, 1986; Kuhlemeier et al., *Mol Gen Genet* 212:405-411, 1988; Mascarenhas et al., *Plant Mol. Biol.* 15:913-920, 1990; Sinibaldi and Mettler, In WE Cohn, K Moldave, eds, Progress in Nucleic Acid Research and Molecular Biology, Vol 42. Academic Press, New York, pp 229-257, 1992; Vancanneyt et al., *Mol. Gen. Genet.* 220:245-250, 1990). Therefore, not every intron can be employed to manipulate the gene expression level of non-endogenous genes or endogenous genes in transgenic plants. What characteristics or specific sequence features must be present in an intron sequence in order to enhance the expression rate of a given gene is not known in the prior art, and therefore it is not possible to predict whether a given plant intron, when used heterologously, will cause IME.

As used herein, the term "chimeric" refers to a single DNA molecule produced by fusing a first DNA molecule to a second DNA molecule, where neither the first nor second the DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments, for example the fusion of a promoter to an enhancer element. Thus, the design, construction, and use of chimeric promoters according to the methods disclosed herein for modulating the expression of operably linked transcribable polynucleotide molecules are encompassed by the present invention.

As used herein, the term "variant" refers to a second DNA molecule that is similar in composition, but not identical to, a first DNA molecule, and yet the second DNA molecule still maintains the general functionality, i.e. same or similar expression pattern, of the first DNA molecule. A variant may be a shorter or truncated version of the first DNA molecule and/or an altered version of the sequence of the first DNA molecule, such as one with different restriction enzyme sites and/or internal deletions, substitutions, and/or insertions. A "variant" may also encompass a regulatory element having a nucleotide sequence comprising a substitution, deletion, and/or insertion of one or more nucleotides of a reference sequence, wherein the derivative regulatory element has more or less or equivalent transcriptional or translational activity than the corresponding parent regulatory molecule. The regulatory element "variants" will also encompass variants arising from mutations that naturally occur in bacterial and plant cell transformation. In the present invention, a polynucleotide sequence may be used to create variants that are similar in composition, but not identical to, the polynucleotide sequence of the original regulatory element, while still maintaining the general functionality, i.e. same or similar expression pattern, of the original regulatory element. Production of such variants of the present invention is well within the ordinary skill of the art in light of the disclosure and is encompassed within the scope of the present invention. Chimeric regulatory element "variants" comprise the same constituent elements as a reference sequence, but the constituent elements comprising the chimeric regulatory element may be operatively linked by various methods known in the art, such as restriction enzyme digestion and ligation, ligation independent cloning, modular assembly of PCR products during amplification, or direct chemical synthesis of the regulatory element, as well as other methods known in the art. The resulting chimeric regulatory element "variant" can be comprised of the same, or variants of the same, constituent elements of the reference sequence but differ in the sequence or sequences that comprise the linking sequence or sequences which allow the constituent parts to be operatively linked.

Constructs

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule, where one or more polynucleotide molecule has been linked in a functionally operative manner, i.e. operably linked. As used herein, the term "vector" means any recombinant polynucleotide construct that may be used for the purpose of transformation, i.e. the introduction of heterologous DNA into a host cell. A vector according to the present invention may include an expression cassette or transgene cassette isolated from any of the aforementioned molecules.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. A leader, for example, is operably linked to coding sequence when it is capable of serving as a leader for the polypeptide encoded by the coding sequence.

Constructs of the present invention may be provided, in one embodiment, as double Ti plasmid border DNA constructs that have right border (RB or AGRtu.RB) and left border (LB or AGRtu.LB) regions of the Ti plasmid isolated from Agrobacterium tumefaciens comprising a T-DNA, that along with transfer molecules provided by the A. tumefaciens cells that permit the integration of the T-DNA into the genome of a plant cell (see, for example, U.S. Pat. No. 6,603,061). The constructs may also contain the plasmid backbone DNA segments that provide replication function and antibiotic selection in bacterial cells, for example, an Escherichia coli origin of replication such as ori322, a broad host range origin of replication such as oriV or oriRi, and a coding region for a selectable marker such as Spec/Strp that encodes a Tn7 aminoglycoside adenyltransferase (aadA) conferring resistance to spectinomycin or streptomycin, or a gentamicin (Gm, Gent) selectable marker gene. For plant transformation, the host bacterial strain is often A. tumefaciens ABI, C58, or LBA4404; however, other strains known to those skilled in the art of plant transformation can function in the present invention.

Methods are known in the art for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells are well known to one skilled in the art (see, for example, Molecular Cloning: A Laboratory Manual, 3rd edition Volumes 1, 2, and 3, J. Sambrook, D. W. Russell, and N. Irwin, Cold Spring Harbor Laboratory Press, 2000). Methods for making recombinant vectors particularly suited to plant transformation include, without limitation, those described in U.S. Pat. Nos. 4,971,908; 4,940,835; 4,769,061; and 4,757,011 in their entirety. These types of vectors have also been reviewed in the scientific literature (see, for example, Rodriguez, et al., Vectors: A Survey of Molecular Cloning Vectors and Their Uses, Butterworths, Boston, 1988; and Glick et al., Methods in Plant Molecular Biology and Biotechnology, CRC Press, Boca Raton, Fla., 1993). Typical vectors useful for expression of nucleic acids in higher plants are well known in the art and include vectors derived from the tumor-inducing (Ti) plasmid of A. tumefaciens (Rogers et al., Methods in Enzymology 153: 253-277, 1987). Other recombinant vectors useful for plant transformation, including the pCaMVCN transfer control vector, have also been described in the scientific literature (see, for example, Fromm et al., Proc. Natl. Acad. Sci. USA 82: 5824-5828, 1985).

Various regulatory elements may be included in a construct including any of those provided herein. Any such regulatory elements may be provided in combination with other regulatory elements. Such combinations can be designed or modified to produce desirable regulatory features. In one embodiment, constructs of the present invention comprise at least one regulatory element operably linked to a transcribable polynucleotide molecule operably linked to a 3' transcription termination molecule.

Constructs of the present invention may include any promoter or leader provided herein or known in the art. For example, a promoter of the present invention may be operably linked to a heterologous non-translated 5' leader such as one derived from a heat shock protein gene (see, for example, U.S. Pat. Nos. 5,659,122 and 5,362,865). Alternatively, a leader of the present invention may be operably linked to a heterologous promoter such as the Cauliflower Mosaic Virus (CaMV) 35S transcript promoter (see, U.S. Pat. No. 5,352,605).

As used herein, the term "intron" refers to a DNA molecule that may be isolated or identified from the genomic copy of a gene and may be defined generally as a region spliced out during mRNA processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable polynucleotide molecule. A DNA construct may comprise an intron, and the intron may or may not be heterologous with respect to the transcribable polynucleotide molecule sequence. Examples of introns in the art include the rice actin intron (U.S. Pat. No. 5,641,876) and the corn HSP70 intron (U.S. Pat. No. 5,859,347). Further, when modifying intron/exon boundary sequences, it may be preferable to avoid using the nucleotide sequence AT or the nucleotide A just prior to the 5' end of the splice site (GT) and the nucleotide G or the nucleotide sequence TG, respectively, immediately after 3' end of the splice site (AG) to eliminate the potential of unwanted start codons formed during processing of the messenger RNA into the final transcript. The sequence around the 5' or 3' end splice junction sites of the intron can thus be modified in this manner.

As used herein, the term "3' transcription termination molecule" or "3' UTR" refers to a DNA molecule that is used during transcription to produce the 3' untranslated region (3' UTR) of an mRNA molecule. The 3' untranslated region of an mRNA molecule may be generated by specific cleavage and 3' polyadenylation (polyA tail). A 3' UTR may be operably linked to and located downstream of a transcribable polynucleotide molecule and may include polynucleotides that provide a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region (see, Fraley, et al., Proc. Natl. Acad. Sci. USA, 80: 4803-4807, 1983); wheat hsp17 3' region; pea rubisco small subunit 3' region; cotton E6 3' region (U.S. Pat. No. 6,096,950); 3' regions disclosed in WO/0011200 A2; and the coixin 3' UTR (U.S. Pat. No. 6,635,806).

3' UTRs typically find beneficial use for the recombinant expression of specific genes. In animal systems, machinery of 3' UTRs has been well defined (e.g. Zhao et al., Microbiol Mol Biol Rev 63:405-445, 1999; Proudfoot, Nature 322:562-565, 1986; Kim et al., Biotechnology Progress 19:1620-1622, 2003; Yonaha and Proudfoot, EMBO J. 19:3770-3777, 2000; Cramer et al., FEBS Letters 498:179-182, 2001; Kuerstem and Goodwin, Nature Reviews Genetics 4:626-637, 2003). Effective termination of RNA transcription is required to prevent unwanted transcription of trait-unrelated (downstream) sequences, which may interfere with trait performance. Arrangement of multiple gene expression cassettes in local proximity to one another (e.g. within one T-DNA) may cause suppression of gene expression of one or more genes in said construct in comparison to independent insertions (Padidam and Cao, BioTechniques 31:328-334, 2001. This may interfere with achieving adequate levels of expression, for instance in cases where strong gene expression from all cassettes is desired.

In plants, clearly defined polyadenylation signal sequences are not known. Hasegawa et al. (*Plant J.* 33:1063-1072, 2003) were not able to identify conserved polyadenylation signal sequences in both in vitro and in vivo systems in *Nicotiana sylvestris* and to determine the actual length of the primary (non-polyadenylated) transcript. A weak 3' UTR may generate read-through, which may affect the expression of the genes located in neighboring expression cassettes (Padidam and Cao, BioTechniques 31:328-334, 2001). Appropriate control of transcription termination can prevent read-through into sequences (e.g. other expression cassettes) localized downstream and can further allow efficient recycling of RNA polymerase, to improve gene expression. Efficient termination of transcription (release of RNA Polymerase II from the DNA) is prerequisite for re-initiation of transcription and thereby directly affects the overall transcript level. Subsequent to transcription termination, the mature mRNA is released from the site of synthesis and template to the cytoplasm. Eukaryotic mRNAs are accumulated as poly(A) forms in vivo, making it difficult to detect transcriptional termination sites by conventional methods. However, prediction of functional and efficient 3' UTRs by bioinformatics methods is difficult in that there are no conserved sequences to enable easy prediction of an effective 3' UTR.

From a practical standpoint, it may be beneficial that a 3' UTR used in a transgene cassette possesses certain characteristics. For example, a 3' UTR useful in accordance with the present invention may efficiently and effectively terminate transcription of the transgene and prevent read-through of the transcript into any neighboring DNA sequence, which can be comprised of another transgene cassette, as in the case of multiple cassettes residing in one T-DNA, or the neighboring chromosomal DNA into which the T-DNA has inserted. The 3' UTR optimally should not cause a reduction in the transcriptional activity imparted by the promoter, leader, and introns that are used to drive expression of the transgene. In plant biotechnology, the 3' UTR is often used for priming of amplification reactions of reverse transcribed RNA extracted from the transformed plant and may be used to (1) assess the transcriptional activity or expression of the transgene cassette once integrated into the plant chromosome; (2) assess the copy number of insertions within the plant DNA; and (3) assess zygosity of the resulting seed after breeding. The 3' UTR may also be used in amplification reactions of DNA extracted from the transformed plant to characterize the intactness of the inserted cassette.

3' UTRs useful in providing expression of a transgene in plants may be identified based upon the expression of expressed sequence tags (ESTs) in cDNA libraries made from messenger RNA isolated from seed, flower, or any other tissues derived from, for example, Big bluestem (*Andropogon gerardii*), Plume Grass [*Saccharum ravennae* (*Erianthus ravennae*)], Green bristlegrass (*Setaria viridis*), Teosinte (*Zea mays* subsp. *mexicana*), Foxtail millet (*Setaria italica*), or Coix (*Coix lacryma-jobi*). Using methods known to those skilled in the art, libraries of cDNA may be made from tissues isolated from a plant species using flower tissue, seed, leaf, root, or other plant tissues. The resulting cDNAs are sequenced using various sequencing methods known in the art. The resulting ESTs are assembled into clusters using bioinformatics software such as clc_ref_assemble_complete version 2.01.37139 (CLC bio USA, Cambridge, Mass. 02142). Transcript abundance of each cluster is determined by counting the number of cDNA reads for each cluster. The identified 3' UTRs may be comprised of sequence derived from cDNA sequence, as well as sequence derived from genomic DNA. A cDNA sequence may be used to design primers, which may then be used with GenomeWalker™ (Clontech Laboratories, Inc, Mountain View, Calif.) libraries constructed following the manufacturer's protocol to clone the 3' region of the corresponding genomic DNA sequence to provide a longer termination sequence. Analysis of relative transcript abundance either by direct counts or normalized counts of observed sequence reads for each tissue library may be used to infer properties about patters of expression. For example, some 3' UTRs may be found in transcripts more abundant in root tissue rather than leaf tissue. This suggests that the transcript is highly expressed in root and that the properties of root expression may be attributable to the transcriptional regulation of the promoter, the lead, the introns or the 3' UTR. Empirical testing of 3' UTRs identified by the properties of expression within specific organs, tissues or cell types can result in the identification of 3' UTRs that enhance expression in those specific organs, tissues or cell types.

Constructs and vectors may also include a transit peptide coding sequence that expresses a linked peptide that is useful for targeting of a protein product, particularly to a chloroplast, leucoplast, or other plastid organelle; mitochondria; peroxisome; vacuole; or an extracellular location. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (see, Klee et al., *Mol. Gen. Genet.* 210:437-442, 1987) or the *Petunia hybrida* EPSPS CTP (CTP4) (see, della-Cioppa et al., *Proc. Natl. Acad. Sci. USA* 83:6873-6877, 1986) has been show to target heterologous EPSPS protein sequences to chloroplasts in transgenic plants (see, U.S. Pat. Nos. 5,627,061; 5,633,435; and 5,312,910; and EP 0218571; EP 189707; EP 508909; and EP 924299).

Transcribable Polynucleotide Molecules

As used herein, the term "transcribable polynucleotide molecule" refers to any DNA molecule capable of being transcribed into a RNA molecule, including, but not limited to, those having protein coding sequences and those producing RNA molecules having sequences useful for gene suppression. A "transgene" refers to a transcribable polynucleotide molecule heterologous to a host cell at least with respect to its location in the genome and/or a transcribable polynucleotide molecule artificially incorporated into a host cell's genome in the current or any prior generation of the cell.

A promoter of the present invention may be operably linked to a transcribable polynucleotide molecule that is heterologous with respect to the promoter molecule. As used herein, the term "heterologous" refers to the combination of two or more polynucleotide molecules when such a combination is not normally found in nature. For example, the two molecules may be derived from different species and/or the two molecules may be derived from different genes, e.g. different genes from the same species, or the same genes from different species. A promoter is thus heterologous with respect to an operably linked transcribable polynucleotide molecule if such a combination is not normally found in nature, i.e. that transcribable polynucleotide molecule is not naturally occurring operably linked in combination with that promoter molecule.

The transcribable polynucleotide molecule may generally be any DNA molecule for which expression of a RNA transcript is desired. Such expression of an RNA transcript may result in translation of the resulting mRNA molecule and thus protein expression. Alternatively, for example, a transcribable polynucleotide molecule may be designed to ultimately cause decreased expression of a specific gene or protein. In one embodiment, this may be accomplished by using a transcribable polynucleotide molecule that is oriented in the antisense direction. One of ordinary skill in the art is familiar with using such antisense technology. Briefly, as the antisense transcribable polynucleotide molecule is transcribed, the RNA product hybridizes to and sequesters a complimentary RNA molecule inside the cell. This duplex RNA molecule cannot be translated into a protein by the cell's translational machinery and is degraded in the cell. Any gene may be negatively regulated in this manner.

Thus, in one embodiment of the present invention, a regulatory element may be operably linked to a transcribable polynucleotide molecule on order to modulate transcription of the transcribable polynucleotide molecule at a desired level or in a desired pattern when the construct is integrated in the genome of a plant cell. In one embodiment, the transcribable polynucleotide molecule comprises a protein-coding region of a gene, and the promoter affects the transcription of an RNA molecule that is translated and expressed as an protein product. In another embodiment, the transcribable polynucleotide molecule comprises an antisense region of a gene, and the promoter affects the transcription of an antisense RNA molecule, double stranded RNA or other similar inhibitory RNA molecule in order to inhibit expression of a specific RNA molecule of interest in a target host cell.

Genes of Agronomic Interest

Transcribable polynucleotide molecules in accordance with the present invention may be genes of agronomic interest. As used herein, the term "gene of agronomic interest" refers to a transcribable polynucleotide molecule that, when expressed in a particular plant tissue, cell, or cell type, confers a desirable characteristic, such as one associated with plant morphology, physiology, growth, development, yield, product, nutritional profile, disease or pest resistance, and/or environmental or chemical tolerance. Genes of agronomic interest include, but are not limited to, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein, or any other agent, such as an antisense or RNAi molecule targeting a particular gene for suppression. The product of a gene of agronomic interest may act within the plant in order to cause an effect upon the plant physiology or metabolism, or may be act as a pesticidal agent in the diet of a pest that feeds on the plant.

In one embodiment of the present invention, a promoter is incorporated into a construct such that the promoter is operably linked to a transcribable polynucleotide molecule that is a gene of agronomic interest. The expression of the gene of agronomic interest is desirable in order to confer an agronomically beneficial trait. Without limitation, a beneficial agronomic trait may include, for example, herbicide tolerance, insect control, modified yield, fungal disease resistance, virus resistance, nematode resistance, bacterial disease resistance, plant growth and development, starch production, modified oil production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production, among others. Examples of genes of agronomic interest known in the art include those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. USRE38,446; 6,716,474; 6,663,906; 6,476,295; 6,441,277; 6,423,828; 6,399,330; 6,372,211; 6,235,971; 6,222,098; and 5,716, 837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658; 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; and 6,476, 295), modified oil production (U.S. Pat. Nos. 6,444,876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822, 141; 6,770,465; 6,706,950; 6,660,849; 6,596,538; 6,589, 767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. USRE37,543; 6,228,623; 5,958,745; and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristic or phenotype by encoding an RNA molecule that causes the targeted modulation of gene expression of an endogenous gene, for example via antisense (see for example, U.S. Pat. No. 5,107,065); inhibitory RNA ("RNAi," including modulation of gene expression via mechanisms mediated by miRNA, siRNA, trans-acting siRNA, and phased sRNA, e.g. as described in published applications US 2006/0200878 and US 2008/0066206, and in U.S. patent application Ser. No. 11/974,469); or cosuppression-mediated mechanisms. The RNA may also be a catalytic RNA molecule (e.g. a ribozyme or a riboswitch; see e.g. US 2006/0200878) engineered to cleave a desired endogenous mRNA product. Thus, any transcribable polynucleotide molecule that encodes a transcribed RNA molecule that affects an agronomically important phenotype or morphology change of interest may be useful for the practice of the present invention. Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in plant cells is disclosed in U.S. Pat. Nos. 5,107,065 and 5,759,829, and posttranscriptional gene suppression using a construct with a sense-oriented transcribable polynucleotide molecule to regulate gene expression in plants is disclosed in U.S. Pat. Nos. 5,283,184 and 5,231,020. Expression of a transcribable polynucleotide in a plant cell can also be used to suppress plant pests feeding on the plant cell, for example, compositions isolated from coleopteran pests (U.S. Patent Publication No. US20070124836) and compositions isolated from nematode pests (U.S. Patent Publication No. US20070250947). Plant pests include, but are not limited to arthropod pests, nematode pests, and fungal or microbial pests. Exemplary transcribable polynucleotide molecules for incorporation into constructs of the present invention include, for example, DNA molecules or genes from a species other than the target species or genes that originate with or are present in the same species, but are incorporated into recipient cells by genetic engineering methods rather than classical reproduction or breeding techniques. The type of polynucleotide molecule may include, but is not limited to, a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding β-glucuronidase (GUS, described in U.S. Pat. No. 5,599,670), green fluorescent protein and variants thereof (GFP, described in U.S. Pat. Nos. 5,491,084 and 6,146,826), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4), are well known in the art. Herbicides for which transgenic plant tolerance has been demonstrated and to which the method of the present invention can be applied, may include, but are not limited to: amino-methyl-phosphonic acid, glyphosate, glufosinate, sulfonylureas, imidazolinones, bromoxynil, dalapon, dicamba, cyclohexanedione, protoporphyrinogen oxidase inhibitors, and isoxasflutole herbicides. Transcribable polynucleotide molecules encoding proteins involved in herbicide tolerance are known in the art, and may include, but are not limited to, a transcribable polynucleotide molecule encoding 5-enolpyruvylshikimate-3-phosphate synthase (EPSPS for glyphosate tolerance, described in U.S. Pat. Nos. 5,627,061; 5,633,435; 6,040,497; and 5,094,945); a transcribable polynucleotide molecule encoding a glyphosate oxidoreductase and a glyphosate-N-acetyl transferase (GOX, described in U.S. Pat. No. 5,463,175; GAT, described in U.S. Patent Publication No. 20030083480; and dicamba monooxygenase, described in U.S. Patent Publication No. 20030135879); a transcribable polynucleotide molecule encoding bromoxynil nitrilase (Bxn for Bromoxynil tolerance, described in U.S. Pat. No. 4,810,648); a transcribable polynucleotide molecule encoding phytoene desaturase (crtI) described in Misawa, et al. (*Plant Journal* 4:833-840, 1993; and *Plant Journal* 6:481-489, 1994) for norflurazon tolerance; a transcribable polynucleotide molecule encoding acetohydroxyacid synthase (AHAS, aka ALS) described in Sathasiivan, et al. (*Nucl. Acids Res.* 18:2188-2193, 1990) for tolerance to sulfonylurea herbicides; and the bar gene described in DeBlock, et al. (*EMBO Journal* 6:2513-2519, 1987) for glufosinate and bialaphos tolerance. The promoter molecules of the present invention may express linked transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, aryloxyalkanoate dioxygenases, acetyl CoA carboxylase, glyphosate oxidoreductase, and glyphosate-N-acetyl transferase.

Included within the term "selectable markers" are also genes that encode a secretable marker whose secretion can be detected as a means of identifying or selecting for transformed cells. Examples include markers that encode a secretable antigen that can be identified by antibody interaction, or even secretable enzymes that can be detected catalytically. Selectable secreted marker proteins fall into a number of classes, including small, diffusible proteins which are detectable, (e.g. by ELISA), small active enzymes that are detectable in extracellular solution (e.g., α-amylase, β-lactamase, phosphinothricin transferase), or proteins that are inserted or trapped in the cell wall (such as proteins that include a leader sequence such as that found in the expression unit of extension or tobacco pathogenesis related proteins, also known as tobacco PR-S). Other possible selectable marker genes will be apparent to those of skill in the art and are encompassed by the present invention.

Cell Transformation

The term "transformation" refers to the introduction of nucleic acid into a recipient host. As used herein, the term "host" refers to a bacterium, a fungus, or a plant, including any cells, tissue, organs, or progeny of the bacterium, fungus, or plant. For instance, a host cell according to the present invention may be any cell or organism, such as a plant cell, algae cell, algae, fungal cell, fungi, bacterial cell, insect cell, or the like. In an embodiment, hosts and transformed cells may include cells from: plants, Aspergillus, yeasts, insects, bacteria and algae. Plant tissues and cells of particular interest include, but are not limited to, protoplasts, calli, roots, tubers, seeds, stems, leaves, seedlings, embryos, and pollen.

As used herein, the term "transformed" refers to a cell, tissue, organ, or organism into which a foreign polynucleotide molecule, such as a construct, has been introduced. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic organism as a parent in a cross and exhibiting an altered phenotype resulting from the presence of a foreign polynucleotide molecule. The term "transgenic" refers to a bacterium, fungus, or plant containing one or more heterologous polynucleic acid molecules.

There are many methods for introducing polynucleic acid molecules into plant cells. The method may generally comprise the steps of selecting a suitable host cell, transforming the host cell with a recombinant vector, and obtaining a transformed host cell. Suitable methods include bacterial infection (e.g. *Agrobacterium*), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plant Physiol. Plant Mol. Biol.* 42: 205, 1991).

Technology for introduction of a DNA molecule into cells is well known to those of skill in the art. Methods and materials for transforming plant cells by introducing a plant DNA construct into a plant genome in the practice of this invention can include any of the well-known and demonstrated methods. Any transformation methods may be utilized to transform a host cell with one or more promoters and/or constructs of the present.

Regenerated transgenic plants can be self-pollinated to provide homozygous transgenic plants. Alternatively, pollen obtained from the regenerated transgenic plants may be crossed with non-transgenic plants, preferably inbred lines of agronomically important species. Descriptions of breeding methods that are commonly used for different traits and crops can be found in one of several reference books, see, for example, Allard, Principles of Plant Breeding, John Wiley & Sons, NY, U. of CA, Davis, Calif., 50-98, 1960; Simmonds, Principles of crop improvement, Longman, Inc., NY, 369-399, 1979; Sneep and Hendriksen, Plant breeding perspectives, Wageningen (ed), Center for Agricultural Publishing and Documentation, 1979; Fehr, Soybeans: Improvement, Production and Uses, 2nd Edition, Monograph, 16:249, 1987; Fehr, Principles of variety development, Theory and Technique, (Vol. 1) and Crop Species Soybean (Vol. 2), Iowa State Univ., Macmillan Pub. Co., NY, 360-376, 1987. Conversely, pollen from non-transgenic plants may be used to pollinate the regenerated transgenic plants.

The transformed plants may be analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays. The expression of a transcribable polynucleotide molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used to evaluate transgene expression.

The seeds of plants of this invention may be harvested from fertile transgenic plants and used to grow progeny generations of transformed plants of this invention, including hybrid plant lines comprising the construct of this invention and expressing a gene of agronomic interest.

The present invention also provides for parts of the plants of the present invention. Plant parts, without limitation, include leaves, stems, roots, tubers, seeds, endosperm, ovule, and pollen. The invention also includes and provides transformed plant cells which comprise a nucleic acid molecule of the present invention.

The transgenic plant may pass along the transgenic polynucleotide molecule to its progeny. Progeny includes any regenerable plant part or seed comprising the transgene derived from an ancestor plant. The transgenic plant is preferably homozygous for the transformed polynucleotide molecule and transmits that sequence to all offspring as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immunoprecipitation, and ELISA.

Having now generally described the invention, the same will be more readily understood through reference to the following examples which are provided by way of illustration, and are not intended to be limiting of the present invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

SEQUENCE LISTING

The attached sequence listing includes nucleic acid and amino acid sequences used in the work leading to the claimed invention.

SEQ ID NO: 1 is a nucleic acid sequence of a construct including gateway 35s promoter (from base 1 to base 1239), transit signal peptide (from 1385 to 1558), oleosin (from 1568 to 2086) and OCS (from 2187 to 2897).

SEQ ID NO: 2 is an amino acid sequence of a peptide including a transit signal peptide and oleosin.

SEQ ID NO: 3 is a nucleic acid sequence including gateway 35s promoter (from base 1 to base 1239), transit signal peptide (from 1385 to 1558), truncated oleosin (from 1568 to 1786), GFP (green fluorescence protein) (from 1787 to 2512) and OCS (from 2614 to 3324).

SEQ ID NO: 4 is an amino acid sequence of a transit signal peptide, truncated oleosin and GFP. This corresponds to the so-called HPG protein referred to herein.

SEQ ID NO: 5 is a nucleic acid sequence including gateway 35s promoter (from base 1 to base 1239), transit signal peptide (from 1385 to 1558), truncated oleosin (from 1559 to 1786) and OCS (from 1888 to 2598).

SEQ ID NO: 6 is an amino acid sequence of a transit signal peptide and truncated oleosin. This corresponds to the so-called HP protein referred to herein.

SEQ ID NO: 7 is a nucleic acid sequence including gateway 35s promoter (from base 1 to base 1239), transit signal peptide (from 1385 to 1558), oleosin (from 1568 to 2083), GFP (green fluorescence protein) (from 2084 to 2809) and OCS (from 2913 to 3623).

SEQ ID NO: 8 is an amino acid sequence of a transit signal peptide, oleosin and GFP.

SEQ ID NO: 9 is the amino acid sequence of AtOLE (Part A of FIG. 6).

SEQ ID NO: 10 is the amino acid sequence of the hydrophobic region of AtOLE (Part B of FIG. 6) (corresponding to amino acid residues 45 to 117 of SEQ ID NO: 9).

EXPERIMENTS

The following experiments investigate the effects of transforming a tobacco plant with: (1) a construct comprising a combination of farnesyl pyrophosphate synthase (FPPS) and squalene synthase (SQS), and (2) a construct comprising FPPS, SQS and a compartmenting peptide, namely an oleosin or a designed hydrophobic protein (HPT) derived from the hydrophobic part of oleosin. In the discussion of the experiments, the FPPS and SQS transformants are referred to as "wild-type" (WT) and they are used as a benchmark against which to compare with the FPS/SQS/HPT or FPS/SQS/Oleosin transformants, in order to determine the effect of including a compartmenting peptide, i.e. the HPT or oleosin, in the construct. The results clearly showed that HPT protein improved terpene accumulation. Based on these results, the inventors went on to develop a genetic construct to produce a synthetic protein complex integrated with a compartmenting peptide for droplet formation.

Experiment 1—Protein Redesign

This experiment looks at the protein design for a compartmenting peptide to enable the formation of a chloroplast-originating droplet body. It utilizes a new protein design based upon *Arabidopsis thaliana* Oleosin (AtOLE). FIG. 6 shows the amino acid sequence (A) of AtOLE. The different regions of this sequence are then shown in part (B) of the figure, with the amino acid sequence of the hydrophobic region of AtOLE set out. Finally in part (C) of FIG. 6, vector construction maps of tobacco transformation are shown, using either the full AtOLE sequence or the hydrophobic region of AtOLE. The abbreviations used in FIG. 6 are explained as follows: LB left border, 35S Cauliflower mosaic virus promoter, TP Transit signal peptide, Ter Terminator, and RB Right border.

Experiment 2—Protein Design as Transformed in Planta

This experiment looks at chloroplast-originating droplet bodies formed by transient expression of droplet-forming proteins.

Two genetic constructs were made following the designs shown in FIG. 7, with a construct comprising oleosin as the compartmenting peptide set out in part A of the figure, and a construct comprising a hydrophobic region of oleosin (HPT) set out in part B.

The constructs were designed to link the expression of the compartmenting peptide (i.e. oleosin or HPT) with green fluorescence protein (GFP) so that its location may be ascertained. The distribution of the chlorophyll is shown in the images A1 and B1 (the first image moving left to right). The distribution of the GFP (and oleosin or HPT) is shown in the images A2 and B2 (the second image). The first and second images are merged to form the third and fourth images. As can be seen from the expression images that the distribution of the GFP and therefore of the compartmenting peptide was different for the two different constructs. The distribution of the complexes comprising the full oleosin protein overlapped with the chloroplast, whereas the complexes comprising just the hydrophobic region of the oleosin protein (HPT) generated signals which surround the chloroplast.

Specifically, as aforementioned, these figures allow us to understand the principles of design the hydrophobic protein for droplet formation. Firstly, a hydrophobic region is required which can be from any droplet forming protein including oleosin. Secondly, any major hydrophilic region needs to be removed in order to remove the control of topology. Thirdly, the transit peptide needs to be replaced in order to control the expression of the hydrophobic protein to any targeted organelle, for example to where the key biosynthesis pathway is. The combination of these three aspects will allow targeting of the droplet formation in any organelle so that a particular biosynthesis pathway may be targeted.

Experiment 3—Yield of Squalene (Terpene) by Droplet Design

This experiment looks at the use of a chloroplast-originated droplet body to increase squalene storage.

FIG. 3 shows the squalene yield following transformation of plants with different genetic constructs. WT or G1 is a plant transformed with a construct comprising the farnesyl pyrophosphate synthase and squalene synthase complex (FPPS/SQS). OG is a plant transformed with a construct comprising the farnesyl pyrophosphate synthase and squalene synthase complex (FPPS/SQS) as well as a compartmenting peptide which is an oleosin. HG is a plant transformed with a construct comprising the farnesyl pyrophosphate synthase and squalene synthase complex (FPS/SQS) as well as a compartmenting peptide which is the hydrophobic region of an oleosin.

Figure 3A:
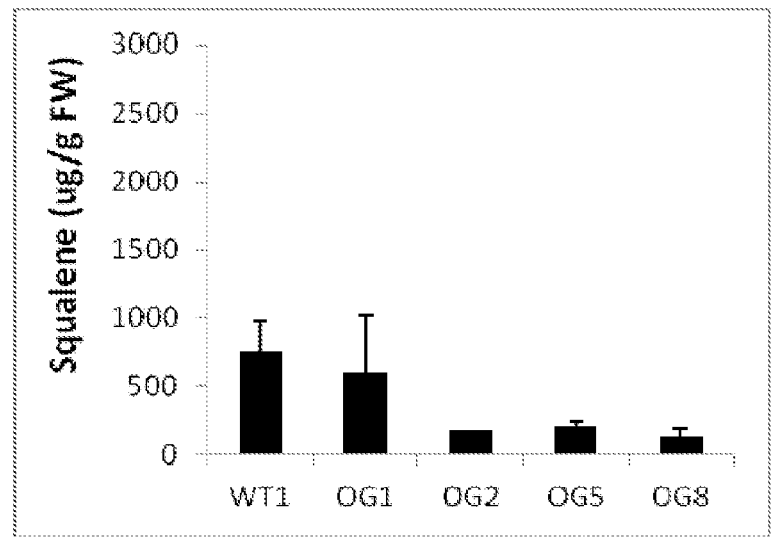
FIG. 3 provides graphs showing the levels of squalene in transformed plants, demonstrating the result of constructs including regular oleosin (OG) and the engineered hydrophobic proteins (HG). WT or G1 designate FPS/SQS transformed plants, OG designates plants transformed with FPS/SQS and regular oleosin and HG designates plants transformed with FPS/SQS and engineered hydrophobic proteins.
Figure 3B:
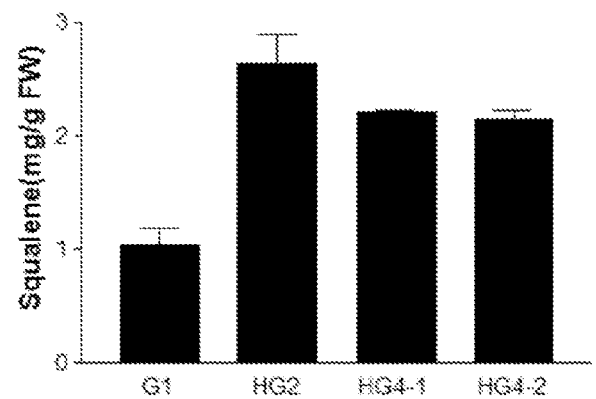
Figure 3C:
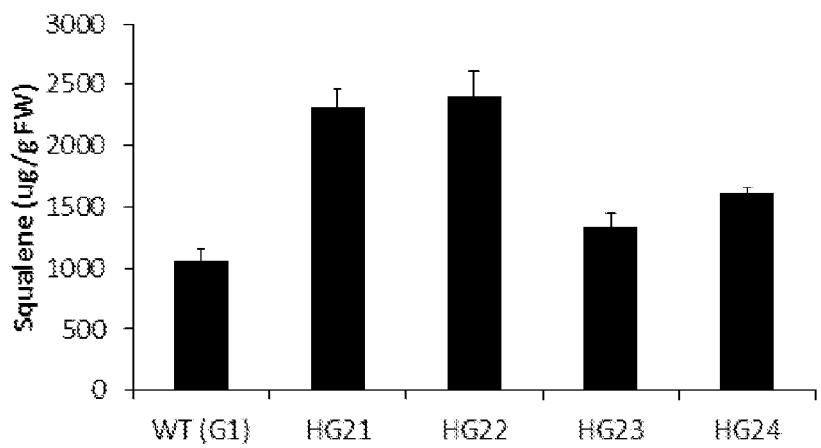

The graphs of FIGS. 3A, 3B and 3C show that expression of the construct comprising a compartmenting peptide which is a hydrophobic region of an oleosin (HPT) effectively increased the terpene storage compared to the WT, allowing the squalene yield to reach approximately 2.5 mg/G of fresh weight (FW). FIG. 3B shows T1 generation and FIG. 3C shows T2 generation.

Taking the information from both FIGS. 3 and 7 together, one can see that the integration of HPT, the specially designed droplet forming compartmenting peptide, with the enzyme complex of FPS/SQS allows the significant improvement of squalene levels.

Basically, the biological product yield increased only in lines that express the designed hydrophobic protein at a high level. These results indicated that our design may lead to the storage of a target biological product, such as a terpene, in the droplets to promote the production.

To put the results shown in FIG. 3 into context, it should be noted that the current record value for squalene yield in a stable transformant of tobacco (using prior art technologies) is 600 µg/G FW. Thus, the yield achieved using the present invention and as presented in this figure is about two to four fold higher than has previously been achieved.

Experiment 4—Plants Produces Droplets Containing Terpene

This experiment looks at the production of droplet bodies in plants transformed with a construct comprising the enzyme complex (FPS/SQS) and the compartmenting peptide which is a hydrophobic region of an oleosin (HPT) as compared to so-called wild type (WT) plants transformed with a construct comprising the enzyme complex (FPS/SQS) only.

In order to further confirm that the synthetic organelle contains squalene, different Raman Spectroscopys were combined. First, the latest SRM (Stimulated Raman Microspectroscopy) was utilized to visualize subcellular structures. Raman microspectroscopy, as a label-free microscopic technique, has been widely used because it offers high chemical specificity. Raman spectroscopy identifies the chemical signature of the compounds by observing the vibration of the chemical bonds. However, the Raman scattering signal is intrinsically weak and often requires long acquisition times. To increase the signal to noise ratio, stimulated Raman scattering (SRS) has been developed to reduce the nonresonant background, and hyperspectral SRS (hsSRS) to acquire many SRS signals at different Raman shifts, thus distinguishing the fine molecular differences.

Figure 4:
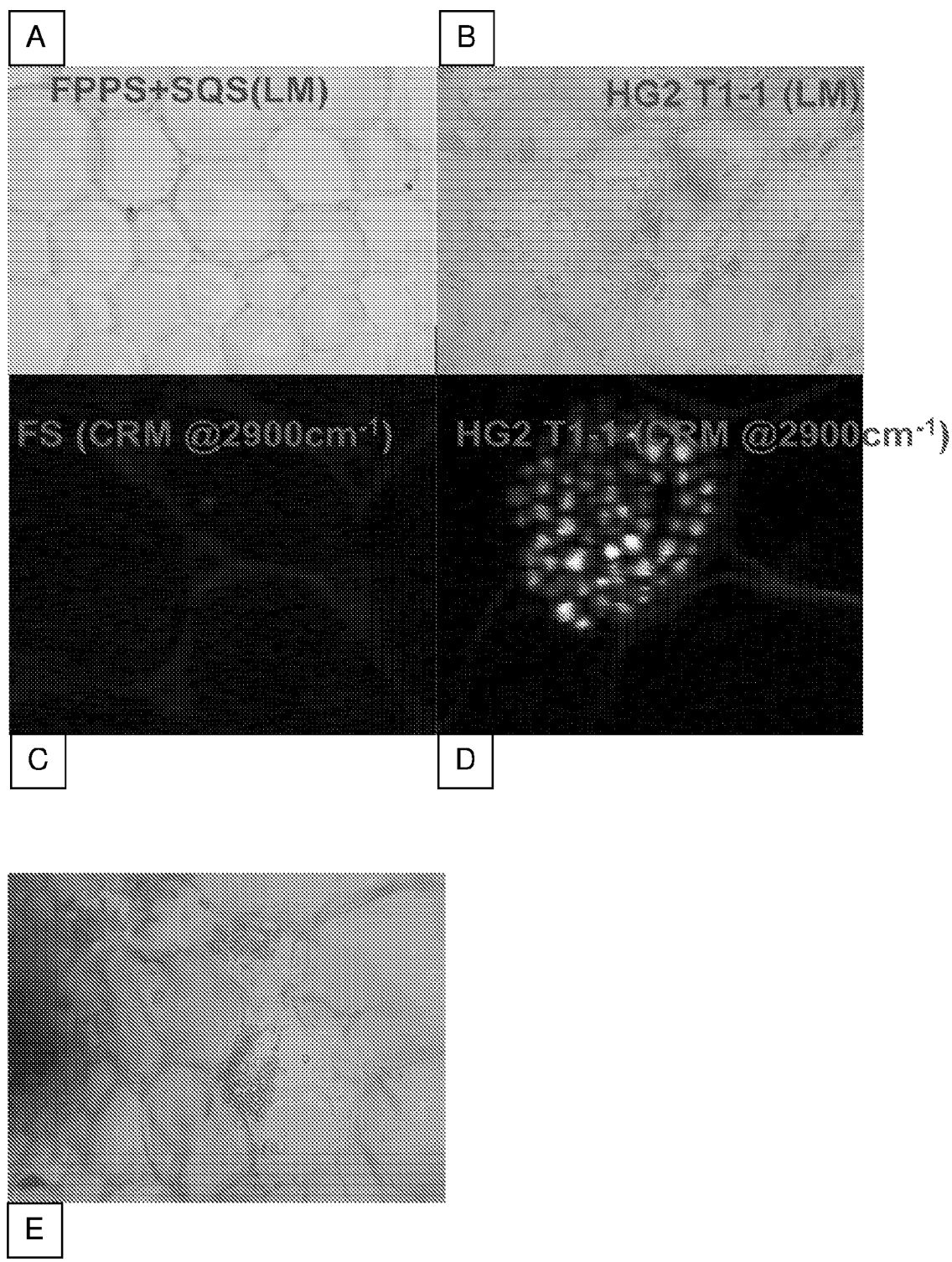
FIG. 4 shows the Coherent anti-stoke Raman Microscopy analysis and light microscopy analysis, where clear droplet can be found from HPT protein engineered plants. A is an optical microscopy image of FPPS-SQS lines stem cross section; B is an image of HPG-FPPS-SQS lines stem section; C is an image of SRS analysis of spectrum 2900 on stem section for FPS-SQS lines; D is an image of SRS analysis of spectrum 2900 on stem section for HPG-FPPS-SQS lines (as shown in B); and E is an image of another HPG-FPPS-SQS line stem cross section.

The Coherent Anti-stoke Raman of FIG. 4 shows that droplet bodies are formed in the HG plants, but not in the WT plants (upper two images designated A (no droplets) and B (droplets), as well as image E (droplets)), thereby demonstrating that the expression of HPT can lead to droplet body formation. Furthermore, FIG. 4 suggests that the droplet bodies contain a terpene hydrocarbon. As shown in the lower right (D) and lower left panels (C), the droplet bodies have 2900 signal band, which indicates that the droplet bodies have the C—H bond, suggesting that the droplet bodies contain hydrocarbons such as squalene. The data clearly show the generation of new droplet bodies and the accumulation of hydrocarbon in the droplet bodies.

Figure 2A:
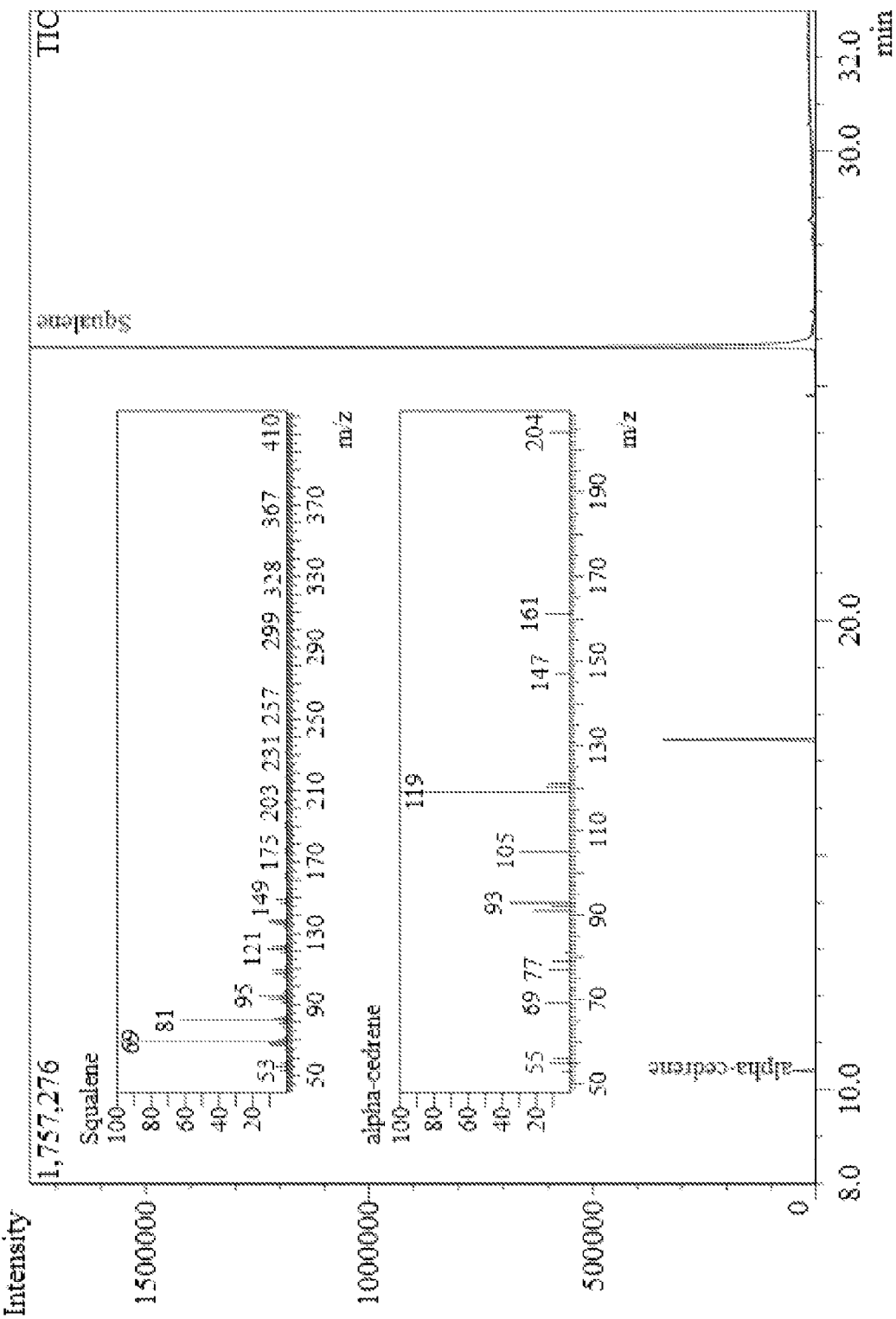
FIG. 2A is a gas chromatography (GC) graph showing the squalene content of a squalene producing tobacco plant transformed according to the present invention.
Figure 2B:
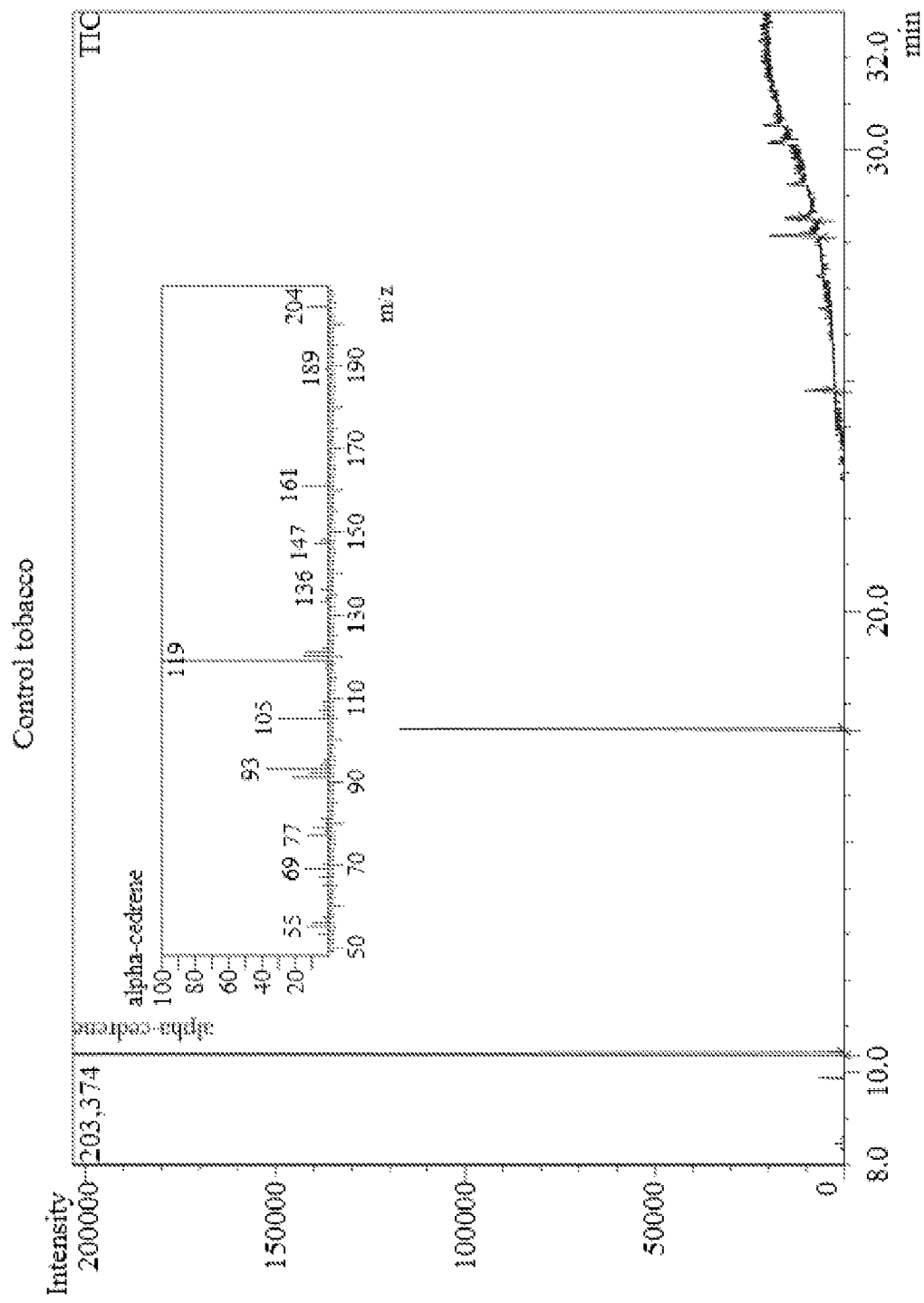
FIG. 2B is a gas chromatography (GC) graph showing the squalene content of a (non-modified) control tobacco plant which does not produce squalene.
Figure 2C:
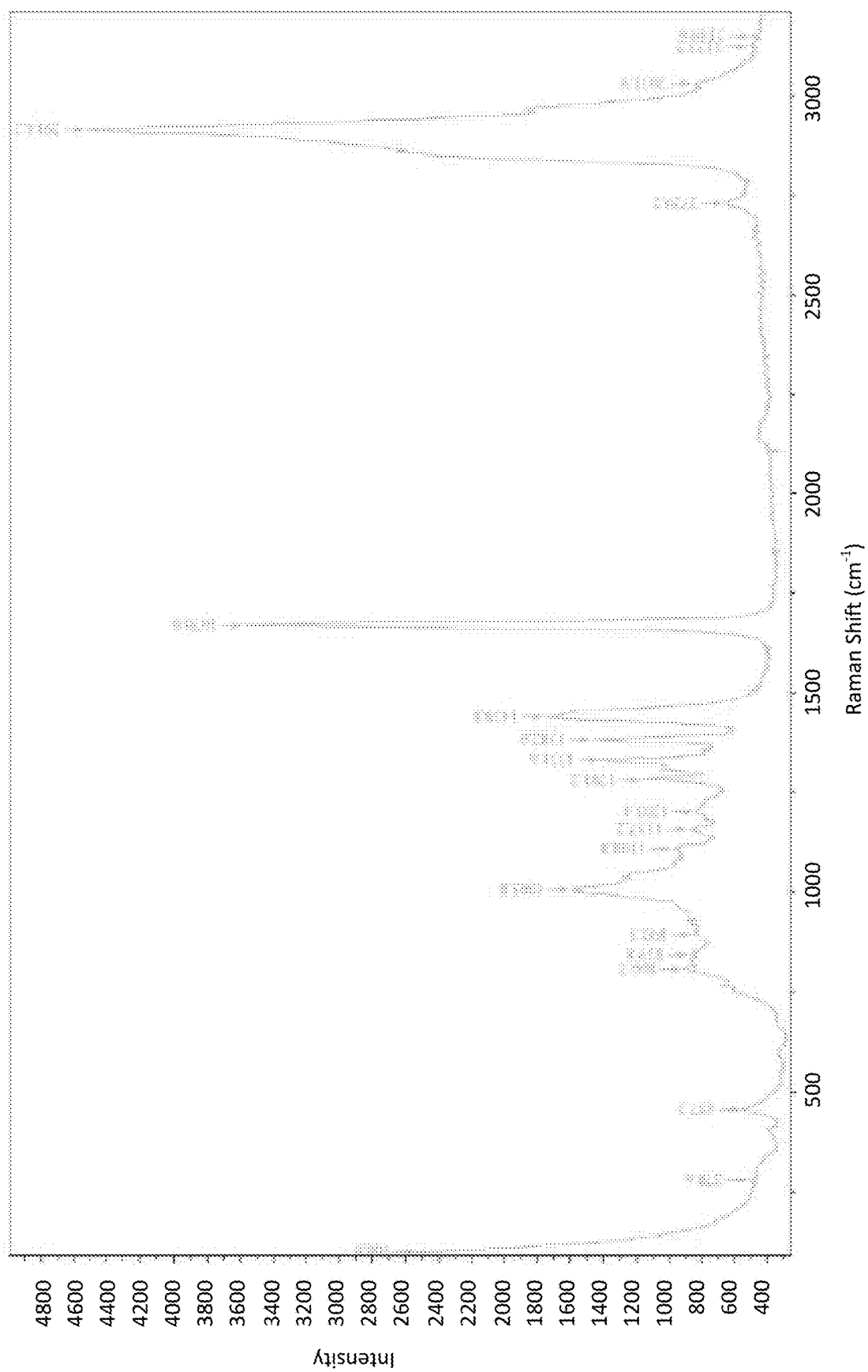
FIG. 2C shows spontaneous Raman spectroscopy used to identify the chemical compounds (squalene) accumulated in the droplets formed in transformed plants.

Because the signature spectrum for squalene at 1670 was too weak to achieve high quality visualization, spontaneous Raman was used to focus on the droplet to obtain the spectra. The result indicated the strong signal at spectrum 1670 (FIG. 2C). The results highlighted that the droplet contains squalene compound. Together with the confocal microscopy data and the squalene yield data, the results indicated that a synthetic droplet has been formed in chloroplast to achieve the increased storage of squalene. The compartmentation of squalene biosynthesis and storage in chloroplast has enabled a significant increase of squalene yield.

The squalene content of the WT plant of image A of FIG. 4 was calculated as approximately 500-600 µg/g, whilst that of the leaf shown in image B was 1.72 mg/g and that of the leaf of image E was 1.88 mg/g.

Taking the data from Experiments 2, and 4, we can clearly see that the expression of an HPT compartmenting peptide improves terpene yield in a transformed plant by promoting the formation of droplet bodies within which the terpene may be stored.

Experiment 5—Increase of Squalene Production by Synthetic Enzyme Complex

This experiment looks at the effect of the formation of a synthetic enzyme complex on squalene production and yield. Terpene yield is shown to be increased by nano-FPPS-SQS machinery.

In FIG. 8, from top to the bottom, there is shown the: Metabolon design; RT-PCR of target genes; and the amount of squalene and derivatives in metabolon transformants vs. separate enzymes.

FIG. 8 shows the increase of terpene level resulting from the expression of a synthetic enzyme complex designed to remove the intermediate effects. As a result, the level of terpene and terpene derivatives are shown to increase significantly.

The results highlight that the synthetic enzyme complex will increase the yield of the biological end product. In particular, this type of enzyme complex will allow removal of the intermediate farnesyl pyrophosphate (FPP) inhibition of the pathway, and further allows the more efficient channeling of the substrate FPP to squalene synthase.

Experiment 6—New Design to Integrate Enzyme Complex with Droplet

In this experiment, the enzyme metabolon is connected to a droplet design to enable a new design where products are channeled to a droplet directly.

Figure 9:
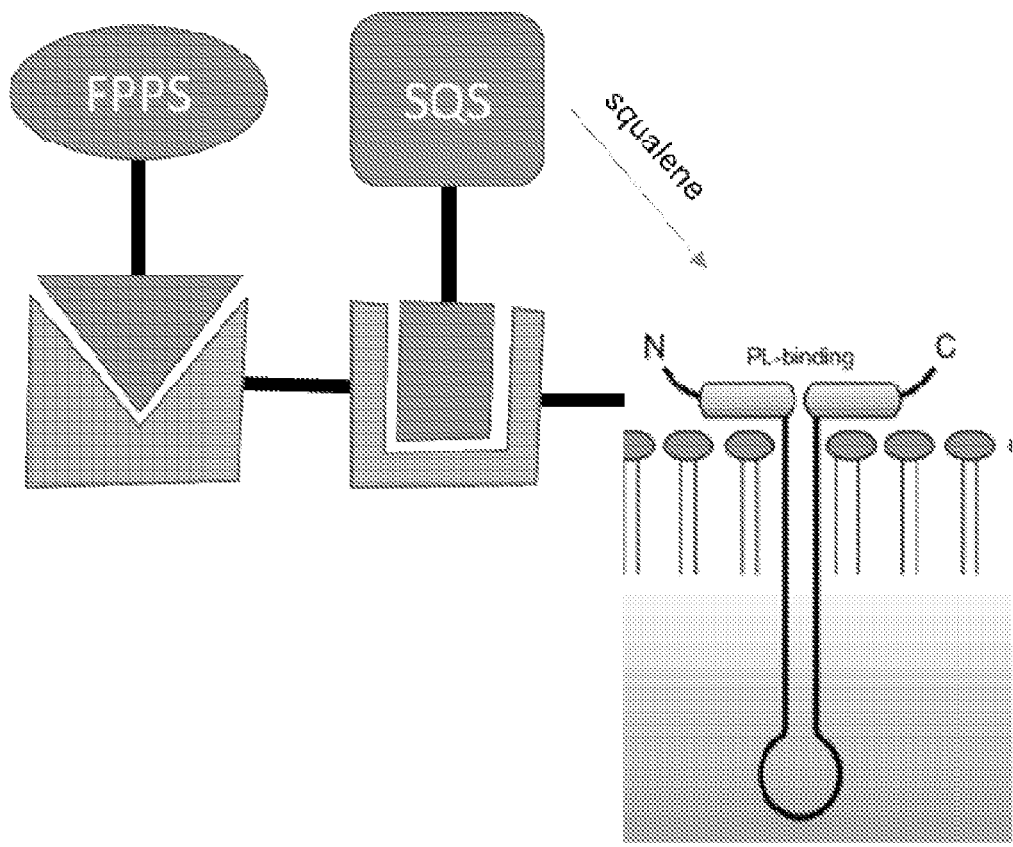
FIG. 9 shows the design of droplet complexes to integrate an enzyme complex with the droplet to achieve ultra-high level of terpene production.

FIG. 9 shows a schematic representation of droplet complexes which are able to integrate an enzyme complex with the droplet to achieve ultra-high level of terpene production.

Based on the previous success, we have designed new way to couple protein complex with droplet formation to further increase the yield.

Experiment 7—Impact on Plant Growth and Development

Figure 10A:
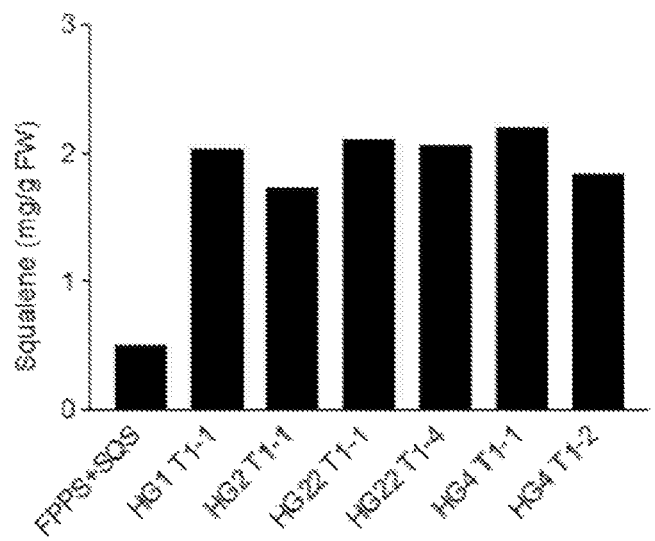
FIGS. 10A to 10C shows the phenotype of transgenic plants.
Figures 10B, 10C:
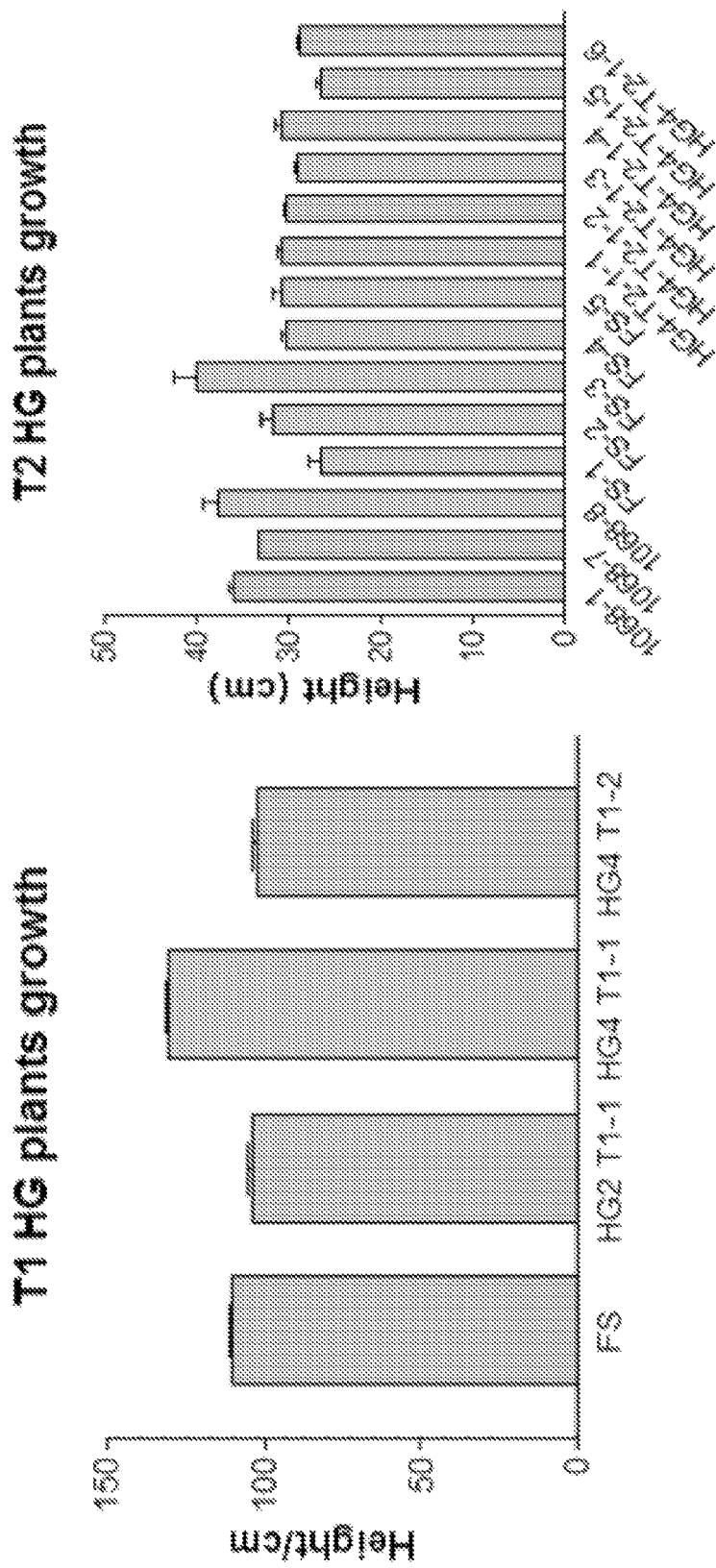

In a previous study, the trichrome-specific FPPS and SQS over-expression was shown to lead to severely dwarf plants and mosaic phenotype. In order to evaluate if the synthetic organelle strategy leads to similar growth defects or not, the growth of HPG-FPPS-SQS, FPS-SQS, and 1068 wild type tobacco plants was compared. As shown in FIGS. 10B and 10C, the height of the HPG transformed tobacco was similar to the wild-type and the FPS-SQS lines. The high accumulation of squalene in HPG-FPS-SQS lines did not result in a significant impact on growth. Overall, the results indicated that synthetic storage organelle can be formed in chloroplast with properly designed hydrophobic proteins, and the compartmentation of biosynthesis and storage of squalene in chloroplast resulted in significant increases in squalene production without impacting plant growth and development. The new strategy thus represents an effective way to increase hydrocarbon compound in planta without impacting plant growth, which could have broad applications.

Methods and Materials
Plant Materials

To obtain sterile tobacco seedlings, tobacco seeds were sterilized with 70% (v/v) ethanol for 30 s and 2% (v/v) sodium hypochlorite solution for 10 min, and rinsed 3 times with sterilized water. Then, the sterilized seeds were germinated on Murashige-Skoog (MS) medium with proper antibiotic selection.

Transformation of Tobacco

The constructs were electroporated into the armed *Agrobacterium tumefaciens* strain GV3101. Tobacco was transformed via the leaf-sac method. Briefly, a culture of *A. tumefaciens* was initiated from glycerol stock and grown overnight at 28° C. with shaking (180 rpm) in liquid Luria-Bertani (LB) medium containing 50 mg/L kanamycin, to mid-log phase ($OD_{600}$=0.5). The *A. tumefaciens* cells were collected by centrifugation for 10 min at 4,000 rpm and resuspended in liquid inoculation medium (containing MS salts, vitamins and 30 g/L sucrose). The *Agrobacterium* cell density was adjusted to an $OD_{600}$ of 1.0 for inoculation.

Excised leaves of 14-day-old G1 tobacco seedlings were used as the explant material for co-cultivation with *A. tumefaciens* GV3101 harboring the expression vectors. The excised explants were dipped into the *A. tumefaciens* culture in liquid inoculation medium for 20 min, blotted dry on sterile filter paper, and incubated in the dark at 25° C. on agar-solidified MS medium with 2,4-D 2 mg/L1. After 2 days of co-cultivation, the explant tissues were washed with sterilized distilled water three times and transferred to MS medium containing salts, vitamins, 6-Benzylaminopurine (BAP) 2 mg/L, sucrose 30 g/L, cefotaxime 500 mg/L, kanamycin 75 mg/L, and plantagar 8 g/L. Putative plants were observed emerging from the wound sites after 3-4 weeks. Selected plants were transferred to rooting media (MS basal salts with IAA 1 mg/L). The rooted plants were transferred to culture vessel for further growth.

Molecular Characterization of Transgenic Tobacco

DNA was extracted from transgenic tobacco using the CTAB method. Total RNA was extracted using the Quick-RNA Miniprep Kit (Zymo Research), and 2 µg of total RNA was reverse transcribed with oligo-dT primers and Superscriptll reverse transcriptase (Life Technology). For PCR reactions, each PCR tube contained 0.2 µM of the forward and reverse primers, 40 µM of each dNTP, 2 µL of DNA template or first-strand cDNA template and 1 unit of Econo Taq DNA polymerase (Lucigen) per 30 µL reactions. Total RNA (without reverse transcription) was used as a negative control for RT-PCR. The PCR reactions were heated to 94° C. for 5 min; 94° C. for 1 min, 55° C. for 1 min, and 72° C. for 1.5 min for 30 cycles; and held at 72° C. for 7 min. From each reaction, 6 µl were loaded on a 1.2% agarose gel, which was stained with ethidium bromide.

Selected T0 tobacco plants were allowed to self and T1 tobacco plants were used for the following analyses.

Squalene Extraction and GC-MS Analysis

Five hundred milligram of positive transgenic tobacco leaf tissue was collected using a 2 cm diameter cork borer. Each sample was grounded with liquid nitrogen, and then extracted with 3 mL hexane. Cedrene was added at a final concentration of 9 ppm to serve as an internal control. The extracts were purified by passing through a 500 mg silica column in a glass pipette plugged with glass wool. Four ml of additional hexane was used to wash the column. The flow-through was analyzed by gas chromatography-mass spectrometry (GC-MS).

GC-MS analysis was run on GCMS-QP2010SE (Shimadzu). One microliter of sample was injected into the GC-MS using an AOC-20i auto-sampler in 10:1 split mode (injector 280° C.) onto a ZB-5MSi fused silica capillary column (30 m×0.25 mm×0.25 µm thickness). The initial oven temperature was 40° C., which was ramped to 120° C. at 20° C./min, then ramped to 200° C. at 6° C./min, then ramped to 260° C. at 20° C./min, and finally ramped to 310° C. for 3 min at 5° C./min. Helium was used as the carrier gas. The ion source was set to 230° C. and the interface was 280° C.

Squalene quantification was performed using selected ions. Peak identification of the compound was performed using direct comparison of the sample mass chromatogram with those of commercially available standard compounds. The quantitative calculations of squalene concentration were based on the peak area ratios relative to those of the standard.

It is important to note that the control line (tobacco 1068) does not produce squalene and the concentration of internal standard cedrene used was 15 ppm, rather than the lower concentration used in the transformed samples (5 ppm).

Confocal Microscopy Imaging

Nile red staining was performed to visualize the synthetic droplets. The plant leaves was vacuum infiltrated with a 2.5 µg/ml Nile red solution in PBS. Then the leaves were washed with PBS twice. Images was acquired from Olympus FV1000 confocal microscope using a ×60 objective.

Plant Growth Measurement

Plant growth was compared based upon two factors. One is plant height which was measured according to stem length. Another is leaf index measurement. Leaf discs were excised from fully expanded leaves at the lower leaves of tobacco. Discs were oven-dried at 70° C. in order to calculate the leaf mass in unit area.

In order to address various issues and advance the art, the entirety of this disclosure shows by way of illustration various embodiments in which the claimed invention(s) may be practiced and provide for superior production and yield of biological products. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future.

The invention claimed is:

1. A genetic construct comprising: a promoter; a coding sequence encoding one or more enzymes whose expression increases production of one or more terpenes in a plant; a coding sequence encoding a compartmenting peptide, wherein expression of the compartmenting peptide leads to formation of a droplet body comprising the one or more terpenes; and a coding sequence encoding a transit signal peptide to direct droplet body formation in chloroplast of the plant.

2. The genetic construct of claim 1, wherein the compartmenting peptide is oleosin, or a functional variant or fragment or orthologue thereof.

3. The genetic construct of claim 1, wherein the one or more enzymes are farnesyl pyrophosphate synthase (FPPS), or squalene synthase (SQS), or both farnesyl pyrophosphate synthase (FPPS) and squalene synthase (SQS).

4. The genetic construct of claim 1, wherein the one or more enzymes comprise squalene synthase (SQS) and one or more upstream enzymes involved in terpene biosynthesis.

5. The genetic construct of claim 4, wherein the upstream enzyme is selected from the group consisting of: farnesyl pyrophosphate synthase (FPPS), geranyl diphosphate synthase (GPPS) and geranylgeranyl diphosphate synthase (GGPPS).

6. The genetic construct of claim 1, further comprising a coding sequence encoding a substrate channeling protein which enhances the production of the one or more terpenes by promoting substrate channeling within the metabolic pathway leading to synthesis of the one or more terpenes.

7. A recombinant vector comprising the genetic construct of claim 1.

8. A method of increasing the yield of the one or more terpenes in a plant compared to the yield of the one or more terpenes in a wild-type plant cultured under the same conditions, the method comprising transforming a plant cell with the genetic construct of claim 1, and regenerating a plant from the transformed cell.

9. A method of producing a transgenic plant which produces a yield of the one or more terpenes which is higher than that of a corresponding wild-type plant cultured under the same conditions, the method comprising transforming a plant cell with the genetic construct of claim 1, and regenerating a plant from the transformed cell.

10. The method of claim 9, wherein the plant is a monocotyledonous or dicotyledonous plant.

11. A transgenic plant comprising the genetic construct of claim 1.

12. A host cell comprising the genetic construct of claim 1.

13. A plant propagation product obtainable from the transgenic plant of claim 11.

14. A plant part containing higher levels of the one or more terpenes than a corresponding part of a wild-type plant cultured under the same conditions, wherein the plant part is produced by the method of claim 8.

\* \* \* \* \*